US007452700B2

(12) United States Patent
Abad et al.

(10) Patent No.: US 7,452,700 B2
(45) Date of Patent: Nov. 18, 2008

(54) METHODS FOR IDENTIFYING NOVEL PESTICIDAL GENE HOMOLOGUES

(75) Inventors: Andre R. Abad, West Des Moines, IA (US); Ronald D. Flannagan, Grimes, IA (US); Bin Hu, Johnston, IA (US); Billy F. McCutchen, Cameron, TX (US); Xiaofeng Sean Yang, Johnston, IA (US); Cao Guo Yu, Irvine, CA (US)

(73) Assignees: Pioneer Hi-Bred International, Inc., Johnston, IA (US); E.I. duPont de Nemours and Company, Wilmington, DE (US)

( * ) Notice: Subject to any disclaimer, the term of this patent is extended or adjusted under 35 U.S.C. 154(b) by 120 days.

(21) Appl. No.: 11/404,741

(22) Filed: Apr. 14, 2006

(65) Prior Publication Data

US 2007/0243536 A1 Oct. 18, 2007

(51) Int. Cl.
*C12P 19/34* (2006.01)
*C12Q 1/68* (2006.01)
*C07H 21/04* (2006.01)

(52) U.S. Cl. ....................... 435/91.2; 435/6; 536/24.32; 536/24.33

(58) Field of Classification Search ....................... None
See application file for complete search history.

(56) References Cited

U.S. PATENT DOCUMENTS

| | | | | |
|---|---|---|---|---|
| 5,204,237 | A | 4/1993 | Gaertner et al. | |
| 5,506,099 | A | 4/1996 | Carozzi et al. | |
| 5,856,144 | A * | 1/1999 | Mierendorf et al. | 435/91.2 |
| 6,593,293 | B1 | 7/2003 | Baum et al. | |
| 2004/0072242 | A1 * | 4/2004 | Hunter et al. | 435/7.1 |

OTHER PUBLICATIONS

Rychlik et al. Optimization of the annealing temperature for DNA amplification in vitro. Nucleic Acids Research 1990; 18(21): 6409-6412.*

Ben-Dov et al. Extended screening by PCR for seven cry-group genes from field-collected strains of *Bacillus thuringiensis*. Applied and Environmental Microbiology 1997; 63(12): 4883-4890.*

Wittwer et al. Continuous fluoroescence monitoring of rapid cycle DNA amplification. BioTechniques 1997; 22: 130, 131, 134-138.*

Ben-Dov et al. Multiplex PCR screening to detect cry9 genes in *Bacillus thuringiensis* strains. Applied and Environmental Microbiology 1999; 65(8): 3714-3716.*

Kuo et al. Identification of novel cry-type genes from *Bacillus thuringiensis* strains on the basis of restriction fragment length polymorphism of the PCR-amplified DNA. Applied and Environmental Microbiology 1996; 62(4): 1369-1377.*

Ibarra et al. Diversity of *Bacillus thuringiensis* strains from Latin America with insecticidal activity against different mosquito species. Applied and Environmental Microbiology 2003; 69(9): 5269-5274.*

* cited by examiner

*Primary Examiner*—Gary Benzion
*Assistant Examiner*—Angela Bertagna
(74) *Attorney, Agent, or Firm*—Alston & Bird LLP

(57) ABSTRACT

Methods and compositions for identifying novel pesticidal gene homologues are provided. Specifically, the methods of the invention comprise systematically designing oligonucleotide primers that are specific for a pesticidal gene of interest and performing successive rounds of PCR amplification of nucleic acid material from a microorganism, particularly a *Bacillus thuringiensis* strain, to identify novel homologues of known pesticidal genes. Oligonucleotide primers that can be used to practice the present methods are further disclosed.

13 Claims, No Drawings

SEQUENCE LISTING

<160> NUMBER OF SEQ ID NOS: 58

<210> SEQ ID NO 1
<211> LENGTH: 2106
<212> TYPE: DNA
<213> ORGANISM: Bacillus thuringiensis

<400> SEQUENCE: 1
atgagtccaa ataatcaaaa tgaatatgaa attatagata tggcaccttc tacatctgta 60
tccaatgatt ctaacagata cccttttgcg agtgatccaa caaatgcatt acaaaatatg 120
aattataaag agtatttaag aatgtctgag ggatatgata gtgaatattc tggctcacct 180
gaagtgctta ttagtgagcg agatgcggtt aagacagcaa tcagtttggt aggtactata 240
ttaggaaaat taggagttcc attggtagga ccgattgtga gcctatatag tacacttatt 300
gatgttttgt ggccaggtgg aaagagtcaa tgggaaattt ttatggaaca agtagaagca 360
cttattaatc aaaaaatagc agaatacgca agggctaagg cacttgcaga attagaaggg 420
ttaggaaata actatcaatt atatttaaca gcacttgaag aatggcagga aaatccaagc 480
agtacaagag tcttacgtga tgttcggaat cgatttgaaa tccttgatag cttatttaca 540
caatatatgc cttcttttcg ggtaacaggt tatgaagtac cattactttc agtatatgcg 600
caagcagcta accttcattt attgttatta aaggacgctt ctatttttgg agaagaatgg 660
gggttctcta caaccgctat taataactat tataatcgtc aaatgagtct tatcgcgcaa 720
tattctgatc attgtgtaca atggtataga actgggttag atcgattaaa aggatcgaat 780
gctaaacaat gggttgaata taaccgcttc cgaagagaaa tgacattatc ggtgttagat 840
attatgacat tatttccaat gtatgacatg cgcacgtacc caatggaaac aaaagcacaa 900
ctaacaaggg aagtatatac agatccaatt ggtgccatag gagcgcaagg ttcttggtat 960
gactcagcac cttctttcaa tactctggaa agtactttta taagaggaaa gcatctattt 1020
gattttataa ctagactctc tatatataca gggcgaagct cattcagtgc tagtaattac 1080
ttaaaaaaat ggatagggca tcaaatatcc tctcaaccta taggcggcag tatacaaact 1140
caaacctatg gcactacgag tggcagttct gttattgcta cgcagcaaat tggctttaca 1200
ggttttgacg tttataagac tttatcaaca gcgggggttc tgtttgctta tacttcgaaa 1260
tattatggcg tatctaaagt tgtttttgat gcgatatatc ctgacaacaa gtataaaaca 1320
acatttactt ataatcctgg atctgaaggt attgcagcgc aagaaaagga ttcagaagtt 1380
gaattgccac cagaaacatt agatcaaccc aattatgagg cgtatagcca taggttgaat 1440
tatgttacat ttattagaaa tccagatgta ccagtatttt cttggacaca tcggagtgcg 1500
gatcgtacga atacagttta ttcagataaa atcactcaaa taccagttgt aaaggccagt 1560
gacggcccta aacctttcgt taacgaagtt ggacactatc ttggtggaga tccaatatca 1620
tttatctctt ctggtagcac tggagtgata aggttaaata taaattcacc attatcccaa 1680
aaataccgtg tgagaattcg ctattgctct tcagttgatt ttgacttaga tgtagttcgt 1740
ggaggcacta ctgtaaataa tggtagattt aacaaaagcg cgcctaacgt cggatggcaa 1800
agtttgaagt atgaaaattt taaatttgca agcttttcta caccttttac atttaatcaa 1860
gctcaagata cattaaaaat aagtgtaagg aattttagtt caatcgtagg aggcagcgta 1920
gtttatatag accgaatcga gctcatccca gtaaatgcaa catatgaggc agaacaagat 1980
ttagattcgg caaagaaagc agtgaatacc ttgtttacga atacaaaaga tggtttacga 2040

```
ccaggggtaa cggattatga agtgaatcaa gcggcaaact tagtgtagct cgagaagccg   2100

aattcc                                                              2106


<210> SEQ ID NO 2
<211> LENGTH: 695
<212> TYPE: PRT
<213> ORGANISM: Artificial Sequence
<220> FEATURE:
<223> OTHER INFORMATION: Predicted amino acid sequence encoded by the
      nucleotide sequence of SEQ ID NO:1

<400> SEQUENCE: 2

Met Ser Pro Asn Asn Gln Asn Glu Tyr Glu Ile Ile Asp Met Ala Pro
 1               5                  10                  15

Ser Thr Ser Val Ser Asn Asp Ser Asn Arg Tyr Pro Phe Ala Ser Asp
            20                  25                  30

Pro Thr Asn Ala Leu Gln Asn Met Asn Tyr Lys Glu Tyr Leu Arg Met
        35                  40                  45

Ser Glu Gly Tyr Asp Ser Glu Tyr Ser Gly Ser Pro Glu Val Leu Ile
    50                  55                  60

Ser Glu Arg Asp Ala Val Lys Thr Ala Ile Ser Leu Val Gly Thr Ile
65                  70                  75                  80

Leu Gly Lys Leu Gly Val Pro Leu Val Gly Pro Ile Val Ser Leu Tyr
                85                  90                  95

Ser Thr Leu Ile Asp Val Leu Trp Pro Gly Gly Lys Ser Gln Trp Glu
            100                 105                 110

Ile Phe Met Glu Gln Val Glu Ala Leu Ile Asn Gln Lys Ile Ala Glu
        115                 120                 125

Tyr Ala Arg Ala Lys Ala Leu Ala Glu Leu Glu Gly Leu Gly Asn Asn
    130                 135                 140

Tyr Gln Leu Tyr Leu Thr Ala Leu Glu Glu Trp Gln Glu Asn Pro Ser
145                 150                 155                 160

Ser Thr Arg Val Leu Arg Asp Val Arg Asn Arg Phe Glu Ile Leu Asp
                165                 170                 175

Ser Leu Phe Thr Gln Tyr Met Pro Ser Phe Arg Val Thr Gly Tyr Glu
            180                 185                 190

Val Pro Leu Leu Ser Val Tyr Ala Gln Ala Ala Asn Leu His Leu Leu
        195                 200                 205

Leu Leu Lys Asp Ala Ser Ile Phe Gly Glu Glu Trp Gly Phe Ser Thr
    210                 215                 220

Thr Ala Ile Asn Asn Tyr Tyr Asn Arg Gln Met Ser Leu Ile Ala Gln
225                 230                 235                 240

Tyr Ser Asp His Cys Val Gln Trp Tyr Arg Thr Gly Leu Asp Arg Leu
                245                 250                 255

Lys Gly Ser Asn Ala Lys Gln Trp Val Glu Tyr Asn Arg Phe Arg Arg
            260                 265                 270

Glu Met Thr Leu Ser Val Leu Asp Ile Met Thr Leu Phe Pro Met Tyr
        275                 280                 285

Asp Met Arg Thr Tyr Pro Met Glu Thr Lys Ala Gln Leu Thr Arg Glu
    290                 295                 300

Val Tyr Thr Asp Pro Ile Gly Ala Ile Gly Ala Gln Gly Ser Trp Tyr
305                 310                 315                 320

Asp Ser Ala Pro Ser Phe Asn Thr Leu Glu Ser Thr Phe Ile Arg Gly
                325                 330                 335

Lys His Leu Phe Asp Phe Ile Thr Arg Leu Ser Ile Tyr Thr Gly Arg
            340                 345                 350
```

-continued

```
Ser Ser Phe Ser Ala Ser Asn Tyr Leu Lys Lys Trp Ile Gly His Gln
        355                 360                 365

Ile Ser Ser Gln Pro Ile Gly Gly Ser Ile Gln Thr Gln Thr Tyr Gly
    370                 375                 380

Thr Thr Ser Gly Ser Ser Val Ile Ala Thr Gln Gln Ile Gly Phe Thr
385                 390                 395                 400

Gly Phe Asp Val Tyr Lys Thr Leu Ser Thr Ala Gly Val Leu Phe Ala
                405                 410                 415

Tyr Thr Ser Lys Tyr Tyr Gly Val Ser Lys Val Val Phe Asp Ala Ile
            420                 425                 430

Tyr Pro Asp Asn Lys Tyr Lys Thr Thr Phe Thr Tyr Asn Pro Gly Ser
        435                 440                 445

Glu Gly Ile Ala Ala Gln Glu Lys Asp Ser Glu Val Glu Leu Pro Pro
    450                 455                 460

Glu Thr Leu Asp Gln Pro Asn Tyr Glu Ala Tyr Ser His Arg Leu Asn
465                 470                 475                 480

Tyr Val Thr Phe Ile Arg Asn Pro Asp Val Pro Val Phe Ser Trp Thr
                485                 490                 495

His Arg Ser Ala Asp Arg Thr Asn Thr Val Tyr Ser Asp Lys Ile Thr
            500                 505                 510

Gln Ile Pro Val Val Lys Ala Ser Asp Gly Pro Lys Pro Phe Val Asn
        515                 520                 525

Glu Val Gly His Tyr Leu Gly Gly Asp Pro Ile Ser Phe Ile Ser Ser
    530                 535                 540

Gly Ser Thr Gly Val Ile Arg Leu Asn Ile Asn Ser Pro Leu Ser Gln
545                 550                 555                 560

Lys Tyr Arg Val Arg Ile Arg Tyr Cys Ser Ser Val Asp Phe Asp Leu
                565                 570                 575

Asp Val Val Arg Gly Gly Thr Thr Val Asn Asn Gly Arg Phe Asn Lys
            580                 585                 590

Ser Ala Pro Asn Val Gly Trp Gln Ser Leu Lys Tyr Glu Asn Phe Lys
        595                 600                 605

Phe Ala Ser Phe Ser Thr Pro Phe Thr Phe Asn Gln Ala Gln Asp Thr
    610                 615                 620

Leu Lys Ile Ser Val Arg Asn Phe Ser Ser Ile Val Gly Gly Ser Val
625                 630                 635                 640

Val Tyr Ile Asp Arg Ile Glu Leu Ile Pro Val Asn Ala Thr Tyr Glu
                645                 650                 655

Ala Glu Gln Asp Leu Asp Ser Ala Lys Lys Ala Val Asn Thr Leu Phe
            660                 665                 670

Thr Asn Thr Lys Asp Gly Leu Arg Pro Gly Val Thr Asp Tyr Glu Val
        675                 680                 685

Asn Gln Ala Ala Asn Leu Val
    690                 695
```

<210> SEQ ID NO 3
<211> LENGTH: 2166
<212> TYPE: DNA
<213> ORGANISM: Bacillus thuringiensis

<400> SEQUENCE: 3

```
atgagtccaa ataatcaaaa tgaatatgaa attatagatg cgacaccttc tacttctgta      60

tccaatgatt ctaacagata cccttttgcg aatgagccaa caaatgcatt acaaaatatg     120

aattataagg attatttaag aatgtctgag ggtatgata gtgaatattc tggttcacct      180
```

-continued

```
ggagcacttg ttagtggaaa acaagcaatt aaggttggaa tcgatattgt cggcaacata    240

ttaggtaagt taggagttcc gtttgctagt cagatagtaa gtttttataa ttttattctc    300

gatcagctat ggccatcaaa ttctgtgagt gtatgggaac agattatgac gctagtggaa    360

gaacttgtag atcaaaaaat aacagaatat gcaagaaata aagcactcgc tgaattaaaa    420

ggattaggag atgctttggg tgtatatcag caatcacttg aagcttggtt ggaaaatcgc    480

aatgacacga gagctagaag tgttgtttct aatcaattta tagccttaga actggatttt    540

gttggagcaa ttccatcctt tgcagtatcc gggcaggaag taccattatt agcagtatat    600

gcacaggctg tgaacatgca cttattgtta ctaagagacg cttctatttt tggagaagag    660

tggggattca catcatctga aatttccact tactacaacc gtcaagtgca actcacttct    720

caatattccg attattgtgt gaagtggtac gataccggtt tacagaaatt aaaaggtacg    780

agcgctgaga gttggctgga gtatcatcaa ttccgcagag agatgacttt catggtatta    840

gatttggttg cattatttcc aaactacgat acacacacgt atccacttga aacaaaggct    900

caacttacac gagaagtata tacggatccg atcgccttta atctttctgg ggcagcgggt    960

ttttgtagcc cttggtcaaa gtatactggt atttcctttt cggagattga aaatgatgta   1020

attcgtccgc ctcatttatt taatctactc agaagtttag agattaatac agttaggggg   1080

acaattttag gtaatactaa agattaccta aactattggt caggtcattc tctacaatat   1140

aattttatag gtaagacaat agtcagggaa agtaattatg gatatcttac ttcagaaaaa   1200

actaggattg aattagacac tagagatatt tttgaaatta attcaactgc cgcaagctta   1260

gcgaattact atcaagagac ttatggtgtg ccagaatcta ggctccattt ggtgagatgg   1320

gctagcccat attatacatc atctcatctt tattctaaaa cacatacaac tggagaaggt   1380

tgtacacaag tttatgaatc aagtgaggaa atacctgtag acagaaccgt accgataaat   1440

gaaggttata gtcacagact atcgtatgtc accgctctct tttccagaa aattattaat    1500

actttttata gaaatggaac tctacctgtc tttgtttgga cacatcgaag tgcagatctt   1560

acaaatacaa tttatccaga tgtaattact caaataccag tggtaaaggc ctatgaattg   1620

ggtagctcca tcttaccaga tagtccatca cctactattg tgccagggcc tggatttaca   1680

gggggggata taatacaatt actggcgaat acaaaaggta tagcaaatat gaattttgaa   1740

attcaagaca ttaataaaga atatattatg agaattcggt atgcttccgc tgcaaatcct   1800

gaattcaata tagctgttgg tactagtgga gaaagagtta gtactagtgc tcaaaaaact   1860

atgaatccag ggatatttt aacatttaat aaatttaatt acgcaacttt ccctcccatt    1920

aaatttaatt caactaaaat ttcgataatg ttaacagcaa gattggctgc ttttgcaagc   1980

acattattgg aaacctatat agatagaatc gaattcatcc cagtagatga aacatacgag   2040

gcggagacag atttagaaac ggcgaagaaa gcagtgaatg ccttgtttac gaatacaaaa   2100

gatggcttac gaccaggcgt aacggattat gaagtgaatc aagcggcaaa cttagtgtag   2160

ctcgag                                                               2166
```

<210> SEQ ID NO 4
<211> LENGTH: 719
<212> TYPE: PRT
<213> ORGANISM: Artificial Sequence
<220> FEATURE:
<223> OTHER INFORMATION: Predicted amino acid sequence encoded by the
nucleotide sequence of SEQ ID NO:3

<400> SEQUENCE: 4

-continued

Met Ser Pro Asn Asn Gln Asn Glu Tyr Glu Ile Ile Asp Ala Thr Pro
1 5 10 15

Ser Thr Ser Val Ser Asn Asp Ser Asn Arg Tyr Pro Phe Ala Asn Glu
20 25 30

Pro Thr Asn Ala Leu Gln Asn Met Asn Tyr Lys Asp Tyr Leu Arg Met
35 40 45

Ser Glu Gly Tyr Asp Ser Glu Tyr Ser Gly Ser Pro Gly Ala Leu Val
50 55 60

Ser Gly Lys Gln Ala Ile Lys Val Gly Ile Asp Ile Val Gly Asn Ile
65 70 75 80

Leu Gly Lys Leu Gly Val Pro Phe Ala Ser Gln Ile Val Ser Phe Tyr
85 90 95

Asn Phe Ile Leu Asp Gln Leu Trp Pro Ser Asn Ser Val Ser Val Trp
100 105 110

Glu Gln Ile Met Thr Leu Val Glu Glu Leu Val Asp Gln Lys Ile Thr
115 120 125

Glu Tyr Ala Arg Asn Lys Ala Leu Ala Glu Leu Lys Gly Leu Gly Asp
130 135 140

Ala Leu Gly Val Tyr Gln Gln Ser Leu Glu Ala Trp Leu Glu Asn Arg
145 150 155 160

Asn Asp Thr Arg Ala Arg Ser Val Val Ser Asn Gln Phe Ile Ala Leu
165 170 175

Glu Leu Asp Phe Val Gly Ala Ile Pro Ser Phe Ala Val Ser Gly Gln
180 185 190

Glu Val Pro Leu Leu Ala Val Tyr Ala Gln Ala Val Asn Met His Leu
195 200 205

Leu Leu Leu Arg Asp Ala Ser Ile Phe Gly Glu Glu Trp Gly Phe Thr
210 215 220

Ser Ser Glu Ile Ser Thr Tyr Tyr Asn Arg Gln Val Gln Leu Thr Ser
225 230 235 240

Gln Tyr Ser Asp Tyr Cys Val Lys Trp Tyr Asp Thr Gly Leu Gln Lys
245 250 255

Leu Lys Gly Thr Ser Ala Glu Ser Trp Leu Glu Tyr His Gln Phe Arg
260 265 270

Arg Glu Met Thr Phe Met Val Leu Asp Leu Val Ala Leu Phe Pro Asn
275 280 285

Tyr Asp Thr His Thr Tyr Pro Leu Glu Thr Lys Ala Gln Leu Thr Arg
290 295 300

Glu Val Tyr Thr Asp Pro Ile Ala Phe Asn Leu Ser Gly Ala Ala Gly
305 310 315 320

Phe Cys Ser Pro Trp Ser Lys Tyr Thr Gly Ile Ser Phe Ser Glu Ile
325 330 335

Glu Asn Asp Val Ile Arg Pro Pro His Leu Phe Asn Leu Leu Arg Ser
340 345 350

Leu Glu Ile Asn Thr Val Arg Gly Thr Ile Leu Gly Asn Thr Lys Asp
355 360 365

Tyr Leu Asn Tyr Trp Ser Gly His Ser Leu Gln Tyr Asn Phe Ile Gly
370 375 380

Lys Thr Ile Val Arg Glu Ser Asn Tyr Gly Tyr Leu Thr Ser Glu Lys
385 390 395 400

Thr Arg Ile Glu Leu Asp Thr Arg Asp Ile Phe Glu Ile Asn Ser Thr
405 410 415

Ala Ala Ser Leu Ala Asn Tyr Tyr Gln Glu Thr Tyr Gly Val Pro Glu
420 425 430

```
Ser Arg Leu His Leu Val Arg Trp Ala Ser Pro Tyr Tyr Thr Ser Ser
        435                 440                 445

His Leu Tyr Ser Lys Thr His Thr Thr Gly Glu Gly Cys Thr Gln Val
    450                 455                 460

Tyr Glu Ser Ser Glu Glu Ile Pro Val Asp Arg Thr Val Pro Ile Asn
465                 470                 475                 480

Glu Gly Tyr Ser His Arg Leu Ser Tyr Val Thr Ala Leu Phe Phe Gln
                485                 490                 495

Lys Ile Ile Asn Thr Phe Tyr Arg Asn Gly Thr Leu Pro Val Phe Val
            500                 505                 510

Trp Thr His Arg Ser Ala Asp Leu Thr Asn Thr Ile Tyr Pro Asp Val
        515                 520                 525

Ile Thr Gln Ile Pro Val Val Lys Ala Tyr Glu Leu Gly Ser Ser Ile
    530                 535                 540

Leu Pro Asp Ser Pro Ser Pro Thr Ile Val Pro Gly Pro Gly Phe Thr
545                 550                 555                 560

Gly Gly Asp Ile Ile Gln Leu Leu Ala Asn Thr Lys Gly Ile Ala Asn
                565                 570                 575

Met Asn Phe Glu Ile Gln Asp Ile Asn Lys Glu Tyr Ile Met Arg Ile
            580                 585                 590

Arg Tyr Ala Ser Ala Ala Asn Pro Glu Phe Asn Ile Ala Val Gly Thr
        595                 600                 605

Ser Gly Glu Arg Val Ser Thr Ser Ala Gln Lys Thr Met Asn Pro Gly
    610                 615                 620

Asp Ile Leu Thr Phe Asn Lys Phe Asn Tyr Ala Thr Phe Pro Pro Ile
625                 630                 635                 640

Lys Phe Asn Ser Thr Lys Ile Ser Ile Met Leu Thr Ala Arg Leu Ala
                645                 650                 655

Ala Phe Ala Ser Thr Leu Leu Glu Thr Tyr Ile Asp Arg Ile Glu Phe
            660                 665                 670

Ile Pro Val Asp Glu Thr Tyr Glu Ala Glu Thr Asp Leu Glu Thr Ala
        675                 680                 685

Lys Lys Ala Val Asn Ala Leu Phe Thr Asn Thr Lys Asp Gly Leu Arg
    690                 695                 700

Pro Gly Val Thr Asp Tyr Glu Val Asn Gln Ala Ala Asn Leu Val
705                 710                 715


<210> SEQ ID NO 5
<211> LENGTH: 22
<212> TYPE: DNA
<213> ORGANISM: Artificial Sequence
<220> FEATURE:
<223> OTHER INFORMATION: Cry8AB_1 forward oligonucleotide primer

<400> SEQUENCE: 5

aaatgcagga atatgggttg ga                                             22


<210> SEQ ID NO 6
<211> LENGTH: 25
<212> TYPE: DNA
<213> ORGANISM: Artificial Sequence
<220> FEATURE:
<223> OTHER INFORMATION: Cry8AB_1 reverse oligonucleotide primer

<400> SEQUENCE: 6

tcatttgaat cttccactgt tgttc                                          25
```

<210> SEQ ID NO 7
<211> LENGTH: 36
<212> TYPE: DNA
<213> ORGANISM: Artificial Sequence
<220> FEATURE:
<223> OTHER INFORMATION: Cry8Aa-36712 TaqMan oligonucleotide probe

<400> SEQUENCE: 7
tgaaatacct ctagatagaa ctgtaccggt agctga 36

<210> SEQ ID NO 8
<211> LENGTH: 22
<212> TYPE: DNA
<213> ORGANISM: Artificial Sequence
<220> FEATURE:
<223> OTHER INFORMATION: Cry8Aa-36711 forward oligonucleotide primer

<400> SEQUENCE: 8
acatacagct ctccaagggt gt 22

<210> SEQ ID NO 9
<211> LENGTH: 27
<212> TYPE: DNA
<213> ORGANISM: Artificial Sequence
<220> FEATURE:
<223> OTHER INFORMATION: Cry8Aa-36713 reverse oligonucleotide primer

<400> SEQUENCE: 9
agaaagaatg ggaggtaata tgagata 27

<210> SEQ ID NO 10
<211> LENGTH: 23
<212> TYPE: DNA
<213> ORGANISM: Artificial Sequence
<220> FEATURE:
<223> OTHER INFORMATION: Cry8Ba-36715 TaqMan oligonucleotide probe

<400> SEQUENCE: 10
atccacttgg cgcggtagat gtg 23

<210> SEQ ID NO 11
<211> LENGTH: 21
<212> TYPE: DNA
<213> ORGANISM: Artificial Sequence
<220> FEATURE:
<223> OTHER INFORMATION: Cry8Ba-36714 forward oligonucleotide primer

<400> SEQUENCE: 11
ggcaacaaca gctcagctta c 21

<210> SEQ ID NO 12
<211> LENGTH: 19
<212> TYPE: DNA
<213> ORGANISM: Artificial Sequence
<220> FEATURE:
<223> OTHER INFORMATION: Cry8Ba-36716 reverse oligonucleotide primer

<400> SEQUENCE: 12
aggtggacga atagccgct 19

<210> SEQ ID NO 13
<211> LENGTH: 30
<212> TYPE: DNA
<213> ORGANISM: Artificial Sequence
<220> FEATURE:
<223> OTHER INFORMATION: Cry8Bb-74500 TaqMan oligonucleotide probe

<400> SEQUENCE: 13

-continued

```
ccttactgta tatgcaatgg cagccaacct                                      30


<210> SEQ ID NO 14
<211> LENGTH: 30
<212> TYPE: DNA
<213> ORGANISM: Artificial Sequence
<220> FEATURE:
<223> OTHER INFORMATION: Cry8Bb-74501 forward oligonucleotide primer

<400> SEQUENCE: 14

cttttagagt gacaaatttt gaagtaccat                                      30


<210> SEQ ID NO 15
<211> LENGTH: 26
<212> TYPE: DNA
<213> ORGANISM: Artificial Sequence
<220> FEATURE:
<223> OTHER INFORMATION: Cry8Bb-74502 reverse oligonucleotide primer

<400> SEQUENCE: 15

acgcgtcctt taataacagt aaatga                                          26


<210> SEQ ID NO 16
<211> LENGTH: 30
<212> TYPE: DNA
<213> ORGANISM: Artificial Sequence
<220> FEATURE:
<223> OTHER INFORMATION: Cry8Bc-74503 TaqMan oligonucleotide probe

<400> SEQUENCE: 16

tacacaggca gccaaccttc atttactgtt                                      30


<210> SEQ ID NO 17
<211> LENGTH: 28
<212> TYPE: DNA
<213> ORGANISM: Artificial Sequence
<220> FEATURE:
<223> OTHER INFORMATION: Cry8Bc-74504 forward oligonucleotide primer

<400> SEQUENCE: 17

caaattttga agtaccattc cttacagt                                        28


<210> SEQ ID NO 18
<211> LENGTH: 23
<212> TYPE: DNA
<213> ORGANISM: Artificial Sequence
<220> FEATURE:
<223> OTHER INFORMATION: Cry8Bc-74505 reverse oligonucleotide primer

<400> SEQUENCE: 18

ccaaaaattg aagcgtcctt taa                                             23


<210> SEQ ID NO 19
<211> LENGTH: 22
<212> TYPE: DNA
<213> ORGANISM: Artificial Sequence
<220> FEATURE:
<223> OTHER INFORMATION: Cry8AB-74990 oligonucleotide primer

<400> SEQUENCE: 19

atgagtccaa ataatcaaaa tg                                              22


<210> SEQ ID NO 20
<211> LENGTH: 25
<212> TYPE: DNA
<213> ORGANISM: Artificial Sequence
```

```
<220> FEATURE:
<223> OTHER INFORMATION: Cry8AB-73695 oligonucleotide primer

<400> SEQUENCE: 20

tctacgtcta caatcaattc tacac                                          25


<210> SEQ ID NO 21
<211> LENGTH: 28
<212> TYPE: DNA
<213> ORGANISM: Artificial Sequence
<220> FEATURE:
<223> OTHER INFORMATION: Cry8AB-75576 oligonucleotide primer

<400> SEQUENCE: 21

ggatccatga gtccaaataa tcaaaatg                                       28


<210> SEQ ID NO 22
<211> LENGTH: 26
<212> TYPE: DNA
<213> ORGANISM: Artificial Sequence
<220> FEATURE:
<223> OTHER INFORMATION: Cry8AB-73694 oligonucleotide primer

<400> SEQUENCE: 22

gcagtgaatg ccttgtttac gaatac                                         26


<210> SEQ ID NO 23
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 23

gcgaatataa gggagtttaa tcaaca                                         26


<210> SEQ ID NO 24
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 24

gcaaatgtag aggaatttaa tcgaca                                         26


<210> SEQ ID NO 25
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 25

gcaaatgtag aagagtttaa tcgaca                                         26


<210> SEQ ID NO 26
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 26

gcgaatgtgg cagagtttaa tcgaca                                         26
```

<210> SEQ ID NO 27
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 27
gcgaatataa tggagtttaa tcaaca 26

<210> SEQ ID NO 28
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 28
gcgaatataa cggagtttaa tcaaca 26

<210> SEQ ID NO 29
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 29
gcgaatataa aggagtttaa tcaaca 26

<210> SEQ ID NO 30
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 30
gcaaatgtag tggaatttaa tcgaca 26

<210> SEQ ID NO 31
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 31
gcaaatgtag cggaatttaa tcgaca 26

<210> SEQ ID NO 32
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 32
gcaaatgtag gggaatttaa tcgaca 26

<210> SEQ ID NO 33
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 33
gcaaatgtag tagagtttaa tcgaca 26

<210> SEQ ID NO 34
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 34
gcaaatgtag cagagtttaa tcgaca 26

<210> SEQ ID NO 35
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 35
gcaaatgtag gagagtttaa tcgaca 26

<210> SEQ ID NO 36
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 36
gcgaatgtgg tagagtttaa tcgaca 26

<210> SEQ ID NO 37
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 37
gcgaatgtgg gagagtttaa tcgaca 26

<210> SEQ ID NO 38
<211> LENGTH: 26
<212> TYPE: DNA
<213> ORGANISM: Artificial Sequence
<220> FEATURE:
<223> OTHER INFORMATION: Cry2A forward oligonucleotide primer

<400> SEQUENCE: 38
gcgaatgtgg aagagtttaa tcgaca 26

<210> SEQ ID NO 39
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 39
accccagttc cagatacaag gata 24

<210> SEQ ID NO 40
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 40
accccagttc cgtgtgcaag gata 24

<210> SEQ ID NO 41
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 41
accccagttc cagatacaac gcta 24

<210> SEQ ID NO 42
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 42
aacccagttc cagatgcaag gata 24

<210> SEQ ID NO 43
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 43
atcccagttc cagatgcaag gata 24

<210> SEQ ID NO 44
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 44
accacagttc cagatgcaag gcta 24

<210> SEQ ID NO 45
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 45
aacccagttc cagatacaag gata 24

<210> SEQ ID NO 46
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 46
aacccagttc cagatgcaag gata 24

<210> SEQ ID NO 47
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 47
atcccagttc cagatacaag gata 24

<210> SEQ ID NO 48
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 48
atcccagttc cagatgcaag gata 24

<210> SEQ ID NO 49
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 49
agcccagttc cagatacaag gata 24

<210> SEQ ID NO 50
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 50
agcccagttc cagatgcaag gata 24

<210> SEQ ID NO 51
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 51
accccagttc cagatacaag gata 24

<210> SEQ ID NO 52
<211> LENGTH: 24
<212> TYPE: DNA
<213> ORGANISM: Artificial Sequence
<220> FEATURE:
<223> OTHER INFORMATION: Cry2A reverse oligonucleotide primer

<400> SEQUENCE: 52
accccagttc cagatgcaag gata 24

<210> SEQ ID NO 53
<211> LENGTH: 23
<212> TYPE: DNA
<213> ORGANISM: Artificial Sequence
<220> FEATURE:
<223> OTHER INFORMATION: Cry3A forward oligonucleotide primer

<400> SEQUENCE: 53

-continued

```
aatcctgtga gttcacgaaa tcc                                          23


<210> SEQ ID NO 54
<211> LENGTH: 23
<212> TYPE: DNA
<213> ORGANISM: Artificial Sequence
<220> FEATURE:
<223> OTHER INFORMATION: Cry3A reverse oligonucleotide primer

<400> SEQUENCE: 54

ttgcaaacga aggcattgaa tta                                          23


<210> SEQ ID NO 55
<211> LENGTH: 99
<212> TYPE: DNA
<213> ORGANISM: Artificial Sequence
<220> FEATURE:
<223> OTHER INFORMATION: Cry3A insert for positive control

<400> SEQUENCE: 55

gatccaatcc tgtgagttca cgaaatccat gggcatgagt ccaaataatc aaaatgaata     60

tgaaattata gatgctaatt caatgccttc gtttgcaac                         99


<210> SEQ ID NO 56
<211> LENGTH: 21
<212> TYPE: DNA
<213> ORGANISM: Artificial Sequence
<220> FEATURE:
<223> OTHER INFORMATION: Cry3C forward oligonucleotide primer

<400> SEQUENCE: 56

ggccaggtga agacccttta a                                            21


<210> SEQ ID NO 57
<211> LENGTH: 21
<212> TYPE: DNA
<213> ORGANISM: Artificial Sequence
<220> FEATURE:
<223> OTHER INFORMATION: Cry3C reverse oligonucleotide primer

<400> SEQUENCE: 57

tttgtcccat gaatccaatg c                                            21


<210> SEQ ID NO 58
<211> LENGTH: 95
<212> TYPE: DNA
<213> ORGANISM: Artificial Sequence
<220> FEATURE:
<223> OTHER INFORMATION: Cry3C insert for positive control

<400> SEQUENCE: 58

gatccggcca ggtgaagacc ctttaaatgg gcatgagtcc aaataatcaa aatgaatatg     60

aaattataga tgcgcattgg attcatggga caaac                             95
```

METHODS FOR IDENTIFYING NOVEL PESTICIDAL GENE HOMOLOGUES

FIELD OF THE INVENTION

The present invention relates to methods and compositions for identifying novel homologues of known pesticidal genes, particularly *Bacillus thuringiensis* Cry genes.

BACKGROUND OF THE INVENTION

Insect pests are a major factor in the loss of the world's agricultural crops. For example, corn rootworm feeding damage and boll weevil damage can be economically devastating to agricultural producers. Insect pest-related crop loss from corn rootworm alone has reached one billion dollars a year.

Traditionally, the primary methods for impacting insect pest populations, such as corn rootworm populations, are crop rotation and the application of broad-spectrum synthetic chemical pesticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternatives to traditional chemical pesticides that present a lower risk of pollution and environmental hazards and provide a greater target specificity than is characteristic of traditional broad-spectrum chemical insecticides.

Certain species of microorganisms of the genus *Bacillus* are known to possess pesticidal activity against a broad range of insect pests including *Lepidoptera, Diptera, Coleoptera, Hemiptera*, and others. *Bacillus thuringiensis* and *Bacillus pppilliae* are among the most successful biocontrol agents discovered to date. Insect pathogenicity has been attributed to strains of: *B. larvae, B. lentimorbus, B. popilliae, B. sphaericus, B. thuringiensis* (Harwook, ed. (1989) *Bacillus* (Plenum Press), p. 306) and *B. cereus* (International Publication No. WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial pesticides, particularly those obtained from *Bacillus* strains, have played an important role in agriculture as alternatives to chemical pest control. Pesticidal proteins isolated from strains of *Bacillus thuringiensis*, known as δ-endotoxins or Cry toxins, are initially produced in an inactive protoxin form. These protoxins are proteolytically converted into an active toxin through the action of proteases in the insect gut. See, Rukmini et al. (2000) *Biochimie* 82:109-116; Oppert (1999) *Arch. Insect Biochem. Phys.* 42:1-12; and Carroll et al. (1997) *J. Invertebrate Pathology* 70:41-49. Proteolytic activation of the toxin can include the removal of the N- and C-terminal peptides from the protein, as well as internal cleavage of the protein. Once activated, the Cry toxin binds with high affinity to receptors on epithelial cells in the insect gut, thereby creating leakage channels in the cell membrane, lysis of the insect gut, and subsequent insect death through starvation and septicemia. See, e.g., Li et al. (1991) *Nature* 353:815-821.

Recently, agricultural scientists have developed crop plants with enhanced insect resistance by genetically engineering crop plants with pesticidal genes to produce pesticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an environmentally friendly alternative to traditional insect-control methods. In addition, potatoes genetically engineered to contain pesticidal Cry toxins have been developed. These successes with genetic engineering have led researchers to search for novel pesticidal genes, particularly Cry genes. Therefore, new methods for efficiently identifying novel homologues of known pesticidal genes are needed in the art.

BRIEF SUMMARY OF THE INVENTION

The present invention provides methods and compositions for identifying novel homologues of known pesticidal genes. The methods disclosed herein permit the rapid and efficient screening of a large number of nucleotide sequences to identify potential pesticidal gene homologues. The methods for identifying novel pesticidal gene homologues comprise systematically designing oligonucleotide primers that are specific for a target group of pesticidal genes of interest and performing multiple rounds of PCR amplification of nucleic acid material from a microorganism of interest. Specifically, a first round of PCR amplification is performed and is intended to amplify both known and novel nucleotide sequences that are homologous to the target group of pesticidal genes of interest. If PCR products are detected in the first round of PCR, a second sample of nucleic acid material from the microorganism is obtained and is subjected to a second round of PCR amplification. The second round of PCR is intended to amplify only known pesticidal genes from the target group. Thus, a microorganism that comprises nucleic acid material that is amplified in the first round of PCR, and not in the second round, comprises potentially novel pesticidal gene homologues. Nucleic acid molecules comprising potentially novel pesticidal gene sequences are cloned and analyzed further. The methods of the invention are further amenable to automation and high throughput screening.

Compositions of the invention include novel isolated polynucleotides, and variants and fragments thereof, comprising nucleotide sequences that are homologous to known pesticidal genes, particularly *Bacillus thuringiensis* Cry genes. Pesticidal polypeptides encoded by the polynucleotides of the invention are also provided. The compositions disclosed herein find use in protecting plants from pests, including insects, fungi, bacteria, nematodes, acarids, protozoan pathogens, animal-parasitic liver flukes, and the like. Oligonucleotide primers that can be used to practice the methods of invention are further provided.

DETAILED DESCRIPTION OF THE INVENTION

The present invention is directed to methods and compositions for identifying novel homologues of known pesticidal genes, particularly *Bacillus thuringiensis* Cry genes. The methods of the invention permit the rapid and efficient screening of a large number of nucleotide sequences to identify potential pesticidal gene homologues. Specifically, the methods for identifying novel pesticidal gene homologues comprise systematically designing oligonucleotide primers specific for a target group of pesticidal genes of interest and performing multiple rounds of PCR amplification of nucleic acid material from a microorganism of interest, particularly from a *B. thuringiensis* strain. In particular embodiments, the designed primers are used in a first round of PCR amplification, which is intended to amplify both known and novel nucleotide sequences that are homologous to the target group of pesticidal genes of interest. If PCR products are detected in the first round of PCR, a second sample of nucleic acid material from the microorganism is obtained and subjected to a second round of PCR amplification. The second round of PCR is intended to amplify only known pesticidal genes. Thus, nucleic acid material from a microorganism of interest that is amplified in the first round of PCR, but not in the second round, comprises a putative novel pesticidal gene homologue. Nucleic acid molecules comprising putative novel pesticidal gene sequences are cloned and analyzed further.

The compositions include novel isolated polynucleotides, and variants and fragments thereof, comprising nucleotide sequences that are homologous to known pesticidal genes, particularly Cry genes, more particularly Cry8 genes. The amino acid sequences comprising the pesticidal polypeptides encoded by the polynucleotides of the invention are also disclosed herein. Oligonucleotide primers that can be used to practice the present methods are further provided.

The methods of the invention are directed to identifying novel homologues of known pesticidal genes. The methods comprise performing multiple rounds of PCR amplification of nucleic acid material, particularly nucleic acid material obtained from a microorganism of interest, to identify novel pesticidal gene homologues. In some aspects of the invention, the nucleic acid material is from a *B. thuringiensis* strain, more particularly plasmid DNA prepared from a *B. thuringiensis* strain. Specifically, the methods comprise designing at least one pair of oligonucleotide primers that is specific for a target group of pesticidal genes of interest, as described herein below. As used herein, "target group of pesticidal genes" refers to any collection of known pesticidal genes for which homologues are sought. The target group of pesticidal genes is selected and defined by the researcher at the outset of the search for novel pesticidal gene homologues. The oligonucleotide primers specific for the target group are mixed with a first sample of nucleic acid material from a microorganism of interest and a DNA polymerase under conditions that are suitable for amplification by PCR. The methods of the present invention further comprise performing a first round of PCR and detecting the presence or absence of PCR amplification products. If PCR products are obtained in the first round of PCR, a second sample of nucleic acid material from the microorganism is obtained and subjected to a second round of PCR using oligonucleotide primers that are specific for all known pesticidal genes in the target group. The oligonucleotide primers used in the second round of PCR are selected based on their ability to amplify known pesticidal genes from the target group and comprise nucleotide sequences that are different from the oligonucleotide primers used in the first round of PCR. Microorganisms that comprise nucleic acid material that is amplified in the first round of PCR and not in the second round of PCR comprise potentially novel homologues of the target group of pesticidal genes of interest. A third sample of nucleic acid material from the microorganism is then obtained and subjected to PCR to clone the putative novel pesticidal gene homologue. Methods for cloning a nucleotide sequence of interest are well known in the art. In a particular embodiment, the oligonucleotide primers used for cloning comprise nucleotide sequences that permit amplification of the toxin domain and the crystal-forming domain of a novel Cry gene. The cloned putative novel homologue is subjected to further analysis, particularly sequence analysis, to confirm novelty.

In some embodiments, the PCR amplification products generated in the first and second rounds of PCR are detected using SYBR® Green and TaqMan® assays, respectively, as described herein below. Putative novel pesticidal gene homologues identified in accordance with the present methods are sequenced and subjected to sequence comparison with known pesticidal genes to assess novelty. Such sequence analyses are well known in the art.

While not intending to be limited to any one mechanism, the oligonucleotide primers used in the first round of PCR are designed to and likely permit the amplification of both known and novel pesticidal genes that are homologous to the target group of pesticidal genes of interest. In contrast, the oligonucleotide primers used in the second round of PCR are selected to specifically amplify only known pesticidal genes from the target group. Thus, microorganisms that comprise nucleic acid material that is only amplified in the first round of PCR, and not in the second round of PCR, may comprise a novel pesticidal gene homologue.

"Pesticidal gene" refers to a nucleotide sequence that encodes a polypeptide that exhibits pesticidal activity. As used herein, the term "pesticidal activity" refers to the ability of a substance, such as a polypeptide, to inhibit the growth, feeding, or reproduction of an insect pest and/or to kill the insect pest. A "pesticidal polypeptide" or "insect toxin" is intended to mean a protein having pesticidal activity. Pesticidal activity can be measured by routine assays known in the art. Such assays include, but are not limited to, pest mortality, pest weight loss, pest repellency, pest attraction, and other behavioral and physical changes of a pest after feeding and exposure to the substance for an appropriate length of time. General procedures include addition of the experimental compound or organism to the diet source in an enclosed container. Assays for assessing pesticidal activity are well known in the art. See, e.g., U.S. Pat. Nos. 6,570,005 and 6,339,144; herein incorporated by reference in their entirety.

The preferred developmental stage for testing for pesticidal activity is larvae or immature forms of an insect of interest. The insects may be reared in total darkness at from about 20° C. to about 30° C. and from about 30% to about 70% relative humidity. Bioassays may be performed as described in Czapla and Lang (1990) *J. Econ. Entomol.* 83(6):2480-2485. Methods of rearing insect larvae and performing bioassays are well known to one of ordinary skill in the art.

In some embodiments of the invention, the target group of pesticidal genes of interest comprises *Bacillus thuringiensis* (*Bt*) genes. "*Bt*" or "*Bacillus thuringiensis*" gene is intended to mean the broader class of genes found in various strains of *Bacillus thuringiensis* that encode *Bt*toxins, which include such toxins as, for example, Cry (crystal) toxins (i.e., δ-endotoxins) and Cyt (cytotoxic) toxins. "Cry toxin" and "Cyt toxin" include pesticidal polypeptides that are homologous to known Cry or Cyt proteins, respectively. Cry genes include nucleotide sequences that encode any polypeptide classified as a Cry toxin, for example, Cry1, Cry2, Cry3, Cry7, Cry8 and Cry9. See, Crickmore et al. (1998) *Microbiol. Molec. Biol. Rev.* 62:807-813 and Crickmore et al. (2004) *Bacillus Thuringiensis* Toxin Nomenclature at lifesci.sussex.ac.uk/Home/Neil_Crickmore/*Bt*, both of which are herein incorporated by reference in their entirety. The *Bt*toxins are a family of pesticidal proteins that are synthesized as protoxins and crystallize as parasporal inclusions. When ingested by an insect pest, the microcrystal structure is dissolved by the alkaline pH of the insect midgut, and the protoxin is cleaved by insect gut proteases to generate the active toxin. The activated *Bt*toxin binds to receptors in the gut epithelium of the insect, causing membrane lesions and associated swelling and lysis of the insect gut. Insect death results from starvation and septicemia. See, e.g., Li et al. (1991) *Nature* 353: 815-821.

The protoxin form of the Cry toxins contains a crystalline forming segment. A comparison of the amino acid sequences of active Cry toxins of different specificities further reveals five highly-conserved sequence blocks. Structurally, the Cry toxins comprise three distinct domains, which are, from the N- to C-terminus: a cluster of seven alpha-helices implicated in pore formation (referred to as "domain 1"), three anti-parallel beta sheets implicated in cell binding (referred to as "domain 2"), and a beta sandwich (referred to as "domain 3"). The location and properties of these domains are known to those of skill in the art. See, for example, Li et al. (1991) supra and Morse et al. (2001) *Structure* 9:409-417.

The original *Bt* toxin nomenclature system classified the toxins on the basis of pesticidal activity profiles. This system has been replaced with a new nomenclature that is based solely on amino acid sequence identity. Under this system, the Cry and Cyt toxins have been grouped into classes or families based on amino acid sequence identity, and the name of the toxin provides information regarding its homology to other sequences. Thus, for example, the Cry2Aa, Cry2Ab, and Cry2Ac toxins, which are members of the Cry2 family, share approximately 80% amino acid sequence identity. Similarly, the Cry8 family toxins Cry8Aa and Cry8Ba share approximately 65% amino acid sequence identity. See Crickmore et al. (1998), supra.

In particular aspects of the invention, designing at least one pair of oligonucleotide primers that is specific for a target group of pesticidal genes of interest comprises designing non-degenerate oligonucleotide primers via a multi-step process. In certain embodiments, an alignment of nucleotide sequences for a target group of pesticidal genes is prepared. Again, the target group of pesticidal genes comprises any collection of known pesticidal genes for which homologues are sought. Pesticidal genes within a target group will generally share a significant level of sequence identity. In certain embodiments, a target group of pesticidal genes may comprise only a few selected members of a particular class or family of pesticidal genes. Thus, for example, a target group of pesticidal genes may comprise Cry8A and Cry8B nucleotide sequences (e.g., Cry8Aa1, Cry8Ba1, Cry8Bb1, and Cry8Bc1). The alignment of nucleotide sequences from a target group of pesticidal genes will comprise the nucleotide sequence for a reference pesticidal gene of interest. "Reference pesticidal gene of interest" is intended to refer to a pesticidal gene within the target group of pesticidal genes that serves as the starting sequence for oligonucleotide primer design, as described herein below.

Designing non-degenerate oligonucleotide primers that are specific for said target group of pesticidal genes of interest further comprises selecting an initial primer length, wherein the initial primer length is between about 15 base pairs (bp) and about 30 bp, for example, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, or 30 bp. In particular embodiments, the initial primer length is selected to be between about 15 bp and 20 bp. A first round of screening for an oligonucleotide primer is then performed by viewing an initial window of contiguous nucleotides within the nucleotide sequence for the reference pesticidal gene of interest. The initial window begins at the S' end of the reference pesticidal gene of interest and is equivalent in length to the initial primer length. The nucleotide sequence within the initial window is reviewed to determine if it possesses the following required sequence features. Thus, an appropriate nucleotide sequence for a non-degenerate oligonucleotide primer:

1) does not have four or more contiguous identical nucleotide residues;

2) has no more than two guanine or cytosine residues within the last five residues of the 3' end of the nucleotide sequence;

3) has a melting temperature $T_m$ of between about 50° C. and about 65° C.;

4) does not form hairpin or dimer structures;

5) is present in all of the nucleotide sequences from the target group of pesticidal genes (i.e., the alignment described herein above); and, 6) is not conserved among nucleotide sequences from non-target group pesticidal genes.

A nucleotide sequence within the initial window is selected for use as an oligonucleotide primer if all of the above sequence features are present. If the nucleotide sequence within the initial window does not possess all of these sequence features, an adjacent window of contiguous nucleotides is selected by moving the initial window by one base pair toward the 3' end of the nucleotide sequence for the reference pesticidal gene of interest. The adjacent window is equivalent in length to the initial primer length. The nucleotide sequence within the adjacent window is reviewed as described above and selected for use as an oligonucleotide primer if all of the sequence features are present. The process is repeated until a nucleotide sequence satisfying all of the above criteria is found or until the entire nucleotide sequence for the reference pesticidal gene of interest is screened. If the entire nucleotide sequence for the reference pesticidal gene of interest is screened and a nucleotide sequence having all of the sequence features is not identified, then additional rounds of screening are performed beginning at the 5' end of the reference pesticidal gene of interest and using a window length that is increased by one base pair from the previous round of screening. Additional rounds of screening are performed as necessary to identify a nucleotide sequence that possesses the required sequence features. A nucleotide sequence satisfying the above sequence requirements is selected and used as an oligonucleotide primer in the first round of PCR.

As used herein above, a nucleotide sequence is "present" in all of the nucleotide sequences from the target group of genes if the identical nucleotide sequence is found in the nucleotide sequence for each and every member of the target group of pesticidal genes. The term "non-target group of pesticidal genes" refers to all pesticidal genes within a particular family of pesticidal genes, excluding those pesticidal genes that have been selected as the target group. For example, if the selected target group of pesticidal genes comprises Cry8A and Cry8B nucleotide sequences, then the corresponding non-target group would comprise all Cry genes except the Cry8A and Cry8B genes. A nucleotide sequence is "not conserved among nucleotide sequences from non-target group pesticidal genes" if it differs from each of the non-target group pesticidal genes by at least two nucleotide residues. In certain aspects of the invention, determining if a nucleotide sequence within a particular window of contiguous nucleotides is not conserved among non-target group pesticidal genes comprises searching the full-length sequence of each gene from the non-target group of pesticidal genes. In some embodiments, the full-length sequence of each pesticidal gene from the non-target group of pesticidal genes is exhaustively searched using the nucleotide sequence within the window as a string search term. That is, if a nucleotide sequence within a window appears anywhere in a non-target group pesticidal gene or if a nucleotide sequence with less than 2 nucleotide residue differences appears anywhere in a non-target group pesticidal gene, then that particular nucleotide sequence within the window will not be selected as an oligonucleotide primer.

A method for identifying novel homologues of a target group of pesticidal genes of interest using mixed oligonucleotide primer pairs is further disclosed. This aspect of the invention comprises designing at least two pairs of oligonucleotide primers, wherein each pair of primers is specific for a distinct sub-group of the target group of pesticidal genes. As discussed above, "target group of pesticidal genes" refers to any collection of known pesticidal genes for which homologues are sought. In this embodiment of the invention, the target group is divided into at least two sub-groups of pesticidal genes of interest. A "sub-group of the target group of pesticidal genes" is intended to mean a narrower subset or division of the target group comprising a particular selection of pesticidal genes from the entire target group. A target group of pesticidal genes will generally be divided into sub-groups on the basis of sequence identity. That is, sub-groups of the target group of pesticidal genes may be organized such that members of each sub-group will share a significant level of sequence identity. For example, in one embodiment, the target group comprises all Cry 2A genes. Exemplary sub-groups of this target group of pesticidal genes comprise Cry2Aa, Cry2Ab, and Cry2Ac genes, respectively. The target group and sub-groups of pesticidal genes of interest are selected and defined by the researcher at the outset of the investigation for novel pesticidal gene homologues. Designing a mixture of oligonucleotide primers specific for sub-groups of a target group of pesticidal genes finds particular use when, because of sequence differences, it is difficult to develop one set of primers that is specific for an entire target group.

Designing a set of mixed oligonucleotide primers is essentially performed as outlined above for non-degenerate primers. Specifically, an alignment for each sub-group of pesticidal genes is prepared, wherein each alignment comprises a nucleotide sequence for a reference pesticidal gene of interest within that sub-group. The reference pesticidal gene of interest for a sub-group serves as the starting sequence for oligonucleotide primer design for that particular sub-group of pesticidal genes. The nucleotide sequence for the reference pesticidal gene of interest is then screened for an oligonucleotide primer sequence by viewing a window of contiguous nucleotides, as described above. A nucleotide sequence that is found in all nucleotide sequences within a particular sub-group (i.e., the alignment) and satisfies the other sequence features described herein above is selected for use as an oligonucleotide primer for that sub-group of pesticidal genes. Oligonucleotide primers specific for each sub-group are similarly designed. The multiple pairs of oligonucleotide primers specific to the particular sub-groups of pesticidal genes are mixed, and the mixture is used in the first round of PCR amplification to identify potentially novel pesticidal gene sequences. If PCR products are detected in the first round of PCR, a second sample of the nucleic acid material from the microorganism is subjected to a second round of PCR using oligonucleotide primers specific for all known pesticidal genes in the target group, as before, to eliminate known pesticidal genes. Putative novel pesticidal gene homologues are cloned and analyzed as described above.

In a further embodiment, degenerate oligonucleotide primers that are specific for a target group of pesticidal genes of interest are used to identify novel pesticidal gene homologues. Specifically, such methods comprise designing a set of degenerate oligonucleotide primers that is specific for the target group of pesticidal genes, selecting at least two pairs of degenerate primers from the set of primers, and using a mixture of these degenerate primers to perform a first round of PCR amplification of the nucleic acid material from the microorganism of interest, as described above. If PCR products are detected in the first round, a second round of PCR is performed using a new sample of nucleic acid material and oligonucleotide primers that are specific for all known pesticidal genes in the target group. If PCR products are detected in the first round and not in the second round, the nucleic acid from the microorganism comprises a potentially novel pesticidal gene homologue. The putative novel homologue is cloned and analyzed further. In a particular embodiment, the putative novel pesticidal gene homologues identified using degenerate primers are compared with the putative novel homologues identified using non-degenerate primers.

While not intending to be limited to any one mechanism, the use of degenerate oligonucleotide primers in some aspects of the invention may facilitate the identification of novel pesticidal gene homologues. A person skilled in the art will recognize that using non-degenerate primers only in the present methods may at times permit the detection of known, but few or no novel, pesticidal genes. That is, the non-degenerate oligonucleotide primers designed as outlined above may be too stringent to amplify some novel pesticidal gene homologues, and, therefore, only known pesticidal genes would be amplified. By designing and using degenerate oligonucleotide primers, however, the stringency is lowered, and the chances of detecting novel pesticidal gene homologues are increased. Moreover, the degenerate primers may permit the identification of more divergent pesticidal gene homologues than could be identified using the more stringent non-degenerate primers.

Methods for designing degenerate oligonucleotide primers are well known in the art. In a particular embodiment, designing a set of oligonucleotide primers that is specific for a target group of pesticidal genes of interest comprises preparing an alignment of nucleotide sequences for a target group of pesticidal genes, selecting a primer length, and viewing a window of contiguous nucleotides within the alignment, wherein the window is equivalent in length to the primer length. A nucleotide sequence that is conserved among all nucleotide sequences from the target group (i.e., the alignment) is identified, and a set of all possible degenerate oligonucleotide primers based on the conserved sequence is designed. With respect to degenerate oligonucleotide primer design, a nucleotide sequence that is "conserved" among all members of a target group will typically contain no more than five nucleotide residue differences. In certain embodiments, a conserved nucleotide sequence will contain only two to three nucleotide residue differences among nucleotide sequences from the target group of pesticidal genes. Thus, degenerate oligonucleotide primers of the invention will generally comprise about two to about five degenerate nucleotides. At least two pairs of degenerate oligonucleotide primers from the set of all possible degenerate primers for a given nucleotide sequence are selected. Each oligonucleotide primer from the set of all possible degenerate primers is optionally reviewed to determine if the nucleotide sequence possesses all of the sequence features listed below. In some embodiments, only degenerate oligonucleotide primers satisfying these requirements are selected:

1) does not have four or more contiguous identical nucleotide residues;

2) has no more than two guanine or cytosine residues within the last five residues of the 3' end of the nucleotide sequence;

3) has a melting temperature $T_m$ of between about 50° C. and about 65° C.;

4) does not form hairpin or dimer structures; and, 5) is not conserved among nucleotide sequences from non-target group pesticidal genes.

Selected degenerate oligonucleotide primers are mixed and used in a first round of PCR amplification of nucleic acid material from a microorganism of interest. In one embodiment, degenerate oligonucleotide primers for the target group of Cry2A genes are designed and used in the methods of the invention. See Example 3 herein below.

One of skill in the art will recognize that the methods for designing oligonucleotide primers, or individual steps within those methods, disclosed herein can be implemented by computer software programs. For example, alignments of nucleotide sequences for a target group of pesticidal genes can be generated by various computer programs known in the art. A person skilled in the art will also appreciate that the methods of the invention can be performed in an automated fashion. The present methods are further amenable to high throughput screening assay formats.

The oligonucleotide primers specific to a pesticidal gene of interest, designed by any of the methods for non-degenerate, mixed, or degenerate primers, are selected to have a thermal melting point or temperature ($T_m$) of between about 50° C. and 65° C. In particular embodiments, the oligonucleotide primers have a $T_m$ of between about 57° C. and 61° C. A number of formulas have been utilized for determining the $T_m$. Any formula for calculating $T_m$ can be used to practice the present methods. For example, a classic algorithm for $T_m$ determination based on nearest-neighbor thermodynamics is as follows:

$$T_m = EH^o/(ES^o + (R \times \ln(Ct))) - 273.15 + 16.6 \log [X]$$

where $EH^o$ and $ES^o$ are the enthalpy and entropy for helix formation, respectively; R is the molar gas constant (1.987 $(cal)(K^{-1})(mol^{-1})$); Ct is the total strand (primer) concentration; and X is the salt concentration. Rychlik et al. (1990) *Nucleic Acid Res.* 18(21):6409-6412.

Moreover, a novel formula for determining $T_m$ has been devised and is disclosed herein below as Formula I. In some embodiments, the $T_m$ of an oligonucleotide primer is calculated using Formula I.

$$T_m = (EH^o/[ES^o + (R \times \ln(Ct))] - 273.15 + 16.6 \log([X])) \times 1.1144 - 14.964 \qquad \text{Formula I}$$

where $EH^o$(enthalpy)=ΣΔH; $ES^o$(entropy)=ΣΔS+0.368×19×1.585; R (molar gas constant)=1.987; *Ct*(total primer concentration)=log(0.00000005/4)×1000; and X (salt concentration $[K^+]$)=0.05.

A person skilled in the art will recognize that the oligonucleotide primers used to practice the methods of the invention are paired oligonucleotide primers such that there are two individual primers per pair (i.e., a forward primer and a reverse primer). One of the primers in each pair is complementary (i.e., capable of hybridizing) to a portion of the 5' strand of the nucleotide sequence for the pesticidal gene of interest (forward primer), while the other is complementary to a portion of the 3' strand (reverse primer). The oligonucleotide primers are designed such that a suitable polymerase will copy the sequence of each strand 3' to each primer to produce amplified copies (i.e., the PCR amplification product). The present methods utilize at least one pair of oligonucleotide primers for PCR amplification. In certain aspects of the invention, a mixture of oligonucleotide primer pairs comprising 2, 3, 4, 5, 6, or more primer pairs is used.

The oligonucleotide primers of the present invention will be of a suitable length to permit amplification of novel pesticidal genes. The individual primers of each pair will typically comprise between about 15 bp and about 30 bp, more particularly between about 20 bp and about 25 bp. The distance between the individual primers in a pair of oligonucleotide primers will also be sufficient to produce PCR products of a detectable length. Thus, in certain aspects of the invention, the forward and reverse primers are selected such that they are complementary to nucleotide sequences within the pesticidal gene of interest that are between about 50 bp and about 150 bp apart.

Nucleic acid material for use in the present methods may be obtained from any organism of interest, particularly a microorganism, more particularly a *B. thuringiensis* strain. The nucleic acid material may comprise, for example, plasmid DNA prepared from a *B. thuringiensis* strain. In some embodiments, obtaining nucleic acid material comprises isolating DNA from a microorganism of interest. In other embodiments, obtaining nucleic acid material comprises isolating mRNA from a microorganism and synthesizing cDNA. The nucleic acid material may comprise, for example, genomic DNA or cDNA. In particular aspects of the invention, the nucleic acid material comprises a plasmid library generated from *B. thuringiensis* strains. When multiple rounds of PCR amplification are performed, a new sample of nucleic acid material from the microorganism may be obtained and used for each round of PCR. Thus, for example, a new DNA plasmid preparation may be prepared from a *B. thuringiensis* strain for use in each round of PCR.

Nucleic acid amplification by PCR is a fundamental molecular biology technique. Methods for performing PCR are well known in the art and can be performed on instrumentation that is commercially available. See, for example, Sambrook et al. (1989) *Molecular Cloning: A Laboratory Manual* (2d ed., Cold Spring Harbor Laboratory Press, Plainview, N.Y.); Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York), all of which are herein incorporated by reference. Briefly, PCR permits the rapid and efficient amplification of nucleic acid material (e.g., DNA from a gene of interest) comprising a target sequence of interest. The nucleic acid material to be amplified, the oligonucleotide primers, and a thermostable DNA polymerase (e.g., Taq polymerase) are mixed under conditions suitable for PCR amplification. PCR reaction mixes further comprise sufficient amounts of the four deoxynucleoside triphosphates and magnesium chloride. The individual reaction components for PCR are commercially available and are offered by a number of companies (e.g., Roche Diagnostics, Qiagen, Promega, Stratagene, etc.). Previously prepared reaction mixtures or "master mixes" to which only the nucleic acid material and the oligonucleotide primers have to be added are also available. PCR is performed for at least a time sufficient to allow for the production of copies of nucleic acid sequences between oligonucleotide primers in a detectable amount.

In particular embodiments, the methods of the invention comprise performing real-time PCR (RT-PCR), more particularly, quantitative RT-PCR. RT-PCR permits the detection of PCR products at earlier stages of the amplification reaction. Specifically, in RT-PCR the quantitation of PCR products relies on the few cycles where the amount of nucleic acid material amplifies logarithmically until a plateau is reached. During the exponential phase, the amount of target nucleic acid material should be doubling every cycle, and there is no bias due to limiting reagents. Methods and instrumentation for performing RT-PCR are well known in the art. See, for example, Bustin (2000) *J. Molec. Endocrinol.* 25:169-193; Freeman et al. (1999) *Biotechniques* 112:124-125; Halford (1999) *Nat. Biotechnol.* 17:835; and Heid et al. (1996) *Genome Res.* 6(10):986-994, all of which are herein incorporated by reference in their entirety. In certain aspects of the invention, both the first and second rounds of PCR amplification comprise performing RT-PCR.

As used herein, "detecting" PCR amplification products comprises any method for detecting the presence, absence, or quantity of nucleic acids amplified by the PCR steps of the present invention. Methods of detection may provide qualitative or quantitative information regarding the level of amplification. Such methods for detecting PCR amplification products are well known in the art and include, for example, ethidium-bromide stained agarose gel electrophoresis, Southern blotting/probe hybridization, and fluorescence assays.

Many different dyes and probes are available for monitoring PCR and detecting PCR products. For example, PCR products generated by RT-PCR amplification can be detected using a variety of fluorescent dyes and oligonucleotide probes covalently labeled with florescent molecules. Such fluorescent entities are capable of indicating the presence of PCR products and providing a signal related to the quantity of PCR products. Moreover, by using continuous fluorescence monitoring of the PCR products, the point at which the signal is detected above background (Ct; cycle threshold) and is in the exponential phase can be determined. The more abundant the template nucleic acid sequence the earlier the Ct is reached.

Double-stranded DNA-specific dyes can be used to detect PCR product formation in any PCR amplification without the need for synthesizing sequence-specific probes. Such dyes bind specifically to double-stranded DNA (dsDNA) and include but are not limited to SYBR® Green, SYBR® Gold®, and ethidium bromide. "SYBR® Green" refers to any of the commercially available SYBR® Green fluorescent dyes, including SYBR® Green I and SYBR® Green II. With dsDNA dyes, product specificity can be increased by analysis of melting curves or by acquiring fluorescence at a high temperature where nonspecific products have melted. See Ririe et al. (1997) *Anal. Biochem.* 245:154-160; Morrison et al. (1998) *BioTechniques* 24:954-962.

Oligonucleotide probes can also be covalently labeled with fluorescent molecules and used to detect PCR products. Hairpin primers (Sunrise® primers), hairpin probes (Molecular Beacons®), and exonuclease probes (TaqMang probes) are dual-labeled florescent oligonucleotides that can be monitored during PCR. These probes depend on fluorescence quenching of a fluorophore by a quencher on the same oligonucleotide. Fluorescence increases when hybridization or exonuclease hydrolysis occurs.

PCR products can also be detected using two oligonucleotides, each labeled with a fluorescent probe. Hybridization of these oligonucleotides to a target nucleic acid brings the two fluorescent probes close together to allow resonance energy transfer to occur. See, for example, Wittwer et al. (1997) *BioTechniques* 22:130-138. Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705.

In certain aspects of the invention, a SYBR® Green florescent dye is used to detect PCR products, more particularly RT-PCR products. As described above, SYBR® Green is a fluorescent dye that binds the minor groove of dsDNA. When SYBR® Green dye binds to dsDNA, the intensity of the fluorescent emission increases. Thus, as more double-stranded PCR products are produced, the SYBR® Green fluorescent signal also increases. In other aspects of the invention, a 5' nuclease assay is used to monitor PCR, particularly RT-PCR, and to detect PCR amplification products. In the 5' nuclease assay, an oligonucleotide probe called a TaqMan® probe is added to the PCR reagent mix. The TaqMang probe comprises a high-energy fluorescent reporter dye at the 5' end (e.g., FAM) and a low-energy quencher dye at the 3' end (e.g., TAMRA). When the probe is intact, the reporter dye's fluorescent emission is suppressed by the close proximity of the quencher. The TaqMan® probe is further designed to anneal to a specific sequence of template between the forward and reverse primers, and, therefore, the probe binds to the template nucleic acid material in the path of the polymerase. PCR amplification results in cleavage and release of the reporter dye from the quencher-containing probe by the nuclease activity of the polymerase. Thus, the fluorescence signal generated from the released reporter dye is proportional to the amount of the PCR product. Methods and instrumentation (e.g., ABI Prism 7700 Detector; Perkin Elmer/Applied Biosytems Division) for performing RT-PCR using SYBR® Green or TaqMan® probes are well known in the art. In particular embodiments, the PCR products from the first and second rounds of PCR amplification are detected using SYBR® Green and TaqMan® assays, respectively.

The compositions of the invention include novel isolated polynucleotides, and variants and fragments thereof, comprising nucleotide sequences that are homologous to known pesticidal genes. Specifically, polynucleotides that are homologous to known Cry8 genes, particularly Cry8A or Cry8B genes, are disclosed herein (SEQ ID NOs:1 and 3). These sequences were identified using the methods of the present invention and the oligonucleotide primers disclosed herein as SEQ ID NOs:5 and 6. The amino acid sequences comprising pesticidal polypeptides encoded by the nucleic acid molecules of the invention are further provided (SEQ ID NOs:2 and 4). The isolated nucleic acid molecules and pesticidal polypeptides find use, for example, in protecting plants from pest-related damage. Compositions also include oligonucleotide primers that can be used in the practice of the methods of the present invention.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the term "oligonucleotide" or "polynucleotide" is not intended to limit the present invention to polynucleotides comprising DNA. Those of ordinary skill in the art will recognize that oligonucleotides and polynucleotides, can comprise ribonucleotides and combinations of ribonucleotides and deoxyribonucleotides. Such deoxyribonucleotides and ribonucleotides include both naturally occurring molecules and synthetic analogues. The oligonucleotides and polynucleotides of the invention also encompass all forms of sequences including, but not limited to, single-stranded forms, double-stranded forms, and the like.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein, "full-length sequence" in reference to a specified polynucleotide or its encoded protein means having the entire nucleic acid sequence or the entire amino acid sequence of a native sequence. "Native sequence" is intended to mean an endogenous sequence, i.e., a non-engineered sequence found in an organism's genome. A full-length polynucleotide encodes the full-length form of the specified protein.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid molecule encoding a protein may comprise non-translated sequences (e.g., introns) within translated regions of the nucleic acid molecule or may lack such intervening non-translated sequences (e.g., as in cDNA).

Fragments and variants of the disclosed polynucleotides and proteins encoded thereby are also encompassed by the present invention. "Fragment" is intended to mean a portion of the polynucleotide or a portion of the amino acid sequence and hence protein encoded thereby. Fragments of a polynucleotide may encode protein fragments that retain the biological activity of the native protein and hence possess pesticidal activity. Alternatively, fragments of a polynucleotide that are useful as hybridization probes generally do not encode fragment proteins retaining biological activity. Thus, fragments of a polynucleotide may range from at least about 20 nucleotides, about 50 nucleotides, about 100 nucleotides, and up to the full-length polynucleotide encoding the proteins of the invention.

A fragment of a pesticidal polynucleotide that encodes a biologically active portion of a pesticidal protein of the invention will encode at least 15, 25, 30, 50, 100, 150, 200, or 250 contiguous amino acids, or up to the total number of amino acids present in a full-length pesticidal protein of the invention. Fragments of a pesticidal polynucleotide that are useful as hybridization probes or PCR primers generally need not encode a biologically active portion of a pesticidal protein.

Thus, a fragment of a pesticidal polynucleotide may encode a biologically active portion of a pesticidal protein, or it may be a fragment that can be used as a hybridization probe or PCR primer using methods disclosed below. A biologically active portion of a pesticidal protein can be prepared by isolating a portion of one of the pesticidal polynucleotides of the invention, expressing the encoded portion of the pesticidal protein (e.g., by recombinant expression in vitro), and assessing the activity of the encoded portion of the pesticidal protein. Polynucleotides that are fragments of a pesticidal nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length pesticidal polynucleotide disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the pesticidal polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a pesticidal protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NOs:2 or 4 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, pesticidal activity as described herein. Such variants may result from, for example, genetic polymorphism or from human manipulation. Biologically active variants of a native pesticidal protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the pesticidal proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the polynucleotides of the invention include both the naturally occurring sequences as well as mutant forms. Likewise, the proteins of the invention encompass both naturally occurring proteins as well as variations and modified forms thereof. Such variants will continue to possess the desired pesticidal activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for pesticidal activity. See, for example, U.S. Pat. Nos. 6,570,005 and 6,339,144, herein incorporated by reference.

Variant polynucleotides and proteins also encompass sequences and proteins derived from a mutagenic and recombinogenic procedure such as DNA shuffling. With such a procedure, one or more different pesticidal protein coding sequences can be manipulated to create a new pesticidal polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the pesticidal gene of the invention and other known pesticidal genes to obtain a new gene coding for a protein with an improved property of interest, such as increased pesticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other microorganisms. In this manner, methods such as PCR, hybridization, and the like can be used to identify such sequences based on their sequence homology to the sequences set forth herein. Sequences isolated based on their sequence identity to the entire pesticidal sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for a pesticidal polypeptide and that hybridize under stringent conditions to the pesticidal sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the pesticidal polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

While the present invention provides more efficient methods for identifying novel homologues of known pesticidal genes, one of skill in the art will recognize that standard methods known in the art can also be used to identify sequences that are homologous to the pesticidal polynucleotides disclosed herein. For example, an entire pesticidal polynucleotide disclosed herein, or one or more portions thereof, may be used as a probe capable of specifically hybridizing to corresponding pesticidal polynucleotides and messenger RNAs. To achieve specific hybridization under a variety of conditions, such probes include sequences that are unique among pesticidal polynucleotide sequences and are optimally at least about 10 nucleotides in length, and most optimally at least about 20 nucleotides in length. Such probes may be used to amplify corresponding pesticidal polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 101° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 110° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. “Equivalent program” is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, “sequence identity” or “identity” in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have “sequence similarity” or “similarity”. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, “percentage of sequence identity” means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Those skilled in the art will recognize that not all compounds or pesticidal genes and polypeptides are equally effective against all pests. The methods of the invention may be used to identify novel pesticidal genes that are effective against a variety of pests. For purposes of the present invention, pests include, but are not limited to, insects, fungi, bacteria, nematodes, acarids, protozoan pathogens, animal-parasitic liver flukes, and the like. The present methods may be used to identify pesticidal genes that display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. These include larvae of the order Lepidoptera, such as armyworms, cutworms, loopers, and heliothines in the family Noctuidae (e.g., fall armyworm (*Spodoptera frugiperda* J. E. Smith), beet armyworm (*Spodoptera exigua* Hübner), bertha armyworm (*Mamestra configurata* Walker), black cutworm (*Agrotis ipsilon* Hufnagel), cabbage looper (*Trichoplusia ni* Hübner), soybean looper (*Pseudoplusia includens* Walker), velvetbean caterpillar (*Anticarsia gemmatalis* Hübner), green cloverworm (*Hypena scabra* Fabricius) tobacco budworm (*Heliothis virescens* Fabricius), granulate cutworm (*Agrotis subterranea* Fabricius), armyworm (*Pseudaletia unipuncta* Haworth) western cutworm (*Agrotis orthogonia* Morrison)); borers, casebearers, webworms, coneworns, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworn (*Herpetogramma licarsisalis* Walker), sunflower moth (*Homoeosoma electellum* Hulst), lesser cornstalk borer (*Elasmopalpus lignosellus* Zeller)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), sunflower bud moth (*Suleima helianthana* Riley)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus), clover leaf weevil (*Hypera punctata* Fabricius), maize billbug (*Sphenophorus maidis* Chittenden)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera* virgifera LeConte), northern corn rootworm (*Diabrotica barberi* Smith & Lawrence); southern corn rootworm (*Diabrotica undecimpunctata* howardi Barber), corn flea beetle (*Chaetocnema pulicaria* Melsheimer), crucifer flea beetle (*Phyllotreta cruciferae* Goeze), grape *colaspis* (*Colaspis brunnea* Fabricius), cereal leaf beetle (*Oulema melanopus* Linnaeus), sunflower beetle (*Zygogramma exclamationis* Fabricius)); beetles from the family Coccinellidae (e.g. Mexican bean beetle (*Epilachna varivestis* Mulsant); chafers and other beetles from the family Scarabaeidae (e.g., Japanese beetle (*Popillia japonica* Newman), northern masked chafer (white grub) (*Cyclocephala borealis* Arrow), southern masked chafer (white grub) (*Cyclocephala immaculata* Olivier), European chafer (*Rhizotrogus majalis* Razoumowsky), white grub (*Phyllophaga crinita* Burmeister), carrot beetle (*Ligyrus gibbosus* De Geer)); carpet beetles from the family Dermestidae; wireworms from the family Elateridae (e.g., *Melanotus* spp., *Conoderus* spp., *Limonius* spp., *Agriotes* spp., *Ctenicera* spp., *Aeolus* spp.); bark beetles from the family Scolytidae and beetles from the family Tenebrionidae (e.g. *Eleodes* spp). In addition it includes: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidea and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae.

Also included are adults and larvae of the order Acari (mites) such as wheat curl mite (*Aceria tosichella* Keifer), brown wheat mite (*Petrobia latens* Müller), spider mites and red mites in the family Tetranychidae (e.g., European red mite (*Panonychus ulmi* Koch), two spotted spider mite (*Tetranychus urticae* Koch), McDaniel mite (*T. mcdanieli* McGregor), carmine spider mite (*T. cinnabarinus* Boisduval), strawberry spider mite (*T. turkestani* Ugarov & Nikolski)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius (migratory grasshopper), *M. differentialis* Thomas (differential grasshopper), *M. femurrubrum* De Geer, (redlegged grasshopper)), American grasshoppers (e.g., *Schistocerca americana* Drury), desert locust (*S. gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafininers (e.g. *Agromyza parvicornis* Loew (corn blotch leafminer)), midges (e.g., *Contarinia sorghicola* Coquillett (sorghum midge), *Mayetiola destructor* Say (Hessian fly), *Sitodiplosis mosellana* Gehin, (wheat midge), *Neolasioptera murtfeldtiana* Felt, (sunflower seed midge)), fruit flies (Tephritidae), frit flies (e.g., *Oscinella frit* Linnaeus), maggots (e.g., *Delia platura* Meigen (seedcorn maggot) and other *Delia* spp., *Meromyza americana* Fitch (wheat stem maggot)), house flies (e.g., *Musca domestica*

Linnaeus), lesser house flies (e.g., *Fannia canicularis Linnaeus, F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman), grass thrips (*Anaphothrips obscrurus* Müller), tobacco thrips (*Frankliniella fusca* Hinds), western flower thrips (*Frankliniella occidentalis* Pergande), soybean thrips (*Neohydatothrips variabilis* Beach), citrus thrips (*Scirthothrips citri* Moulton) and other foliar feeding thrips; insect pests of the order Hymenoptera including sawflies (e.g. wheat stem sawfly (*Cephus cinctus* Norton)), ants (e.g., red carpenter ant (*Camponotus ferrugineus* Fabricius), black carpenter ant (*C. pennsylvanicus* De Geer), Pharaoh ant (*Monomorium pharaonis* Linnaeus), little fire ant (*Wasmannia auropunctata* Roger), fire ant (*Solenopsis geminata* Fabricius), thief ant (*Solenopsis molesta* Say), red imported fire ant (*S. invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*R. hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus* capitis De Geer), body louse (*P. humanus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*C. canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

The present methods may be used to identify pesticidal genes that display activity against agronomic pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrocis medinalis* Guenée (rice leaf roller), *Crambus caliginosellus* Clemens (corn root webworm), *C. teterrellus* Zincken (bluegrass webworm), *Diatraea grandiosella* Dyar (southwestern corn borer), *D. saccharalis* Fabricius (surgarcane borer), *Earias insulana* Boisduval (spiny bollworm), *E. vittella* Fabricius (spotted bollworm), *Helicoverpa armigera* Hübner (American bollworm), *H. zea* Boddie (corn earworm or cotton bollworm), *Heliothis virescens* Fabricius (tobacco budworm), *Herpetogramma licarsisalis* Walker (sod webworm), *Lobesia botrana* Denis & Schiffermüller (European grape vine moth), *Pectinophora gossypiella* Saunders (pink bollworm), *Phyllocnistis citrella* Stainton (citrus leafminer), *Pieris brassicae* Linnaeus (large white butterfly), *P. rapae* Linnaeus (small white butterfly), *Plutella xylostella* Linnaeus (diamondback moth), *Spodoptera exigua* Hübner (beet armyworm), *S. litura* Fabricius (tobacco cutworm, cluster caterpillar), *S. frugiperda* J. E. Smith (fall armyworm), and *Tuta absoluta* Meyrick (tomato leafminer)).

The present methods may be used to identify pesticidal genes that display activity against insect pests from agronomically important members from the order Homoptera including: *Acyrthisiphon pisum* Harris (pea aphid), *Aphis craccivora* Koch (cowpea aphid), *A. fabae* Scopoli (black bean aphid), *A. gossypii* Glover (cotton aphid, melon aphid), *A. maidiradicis* Forbes (corn root aphid), *A. pomi* De Geer (apple aphid), *A. spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Brevicoryne brassicae* Linnaeus (cabbage aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *R. padi* Linnaeus (bird cherry-oat aphid), *Schizaphis graminum* Rondani (greenbug), *Sipha flava* Forbes, (yellow sugarcane aphid), *Sitobion avenae* Fabricius (English grain aphid), *Therioaphis maculata* Buckton (spotted alfalfa aphid), *Toxoptera aurantii* Boyer de Fonscolombe (black citrus aphid), and *T. citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *B. argentifolii* Bellows & Perring (silverleaf whitefly), *Dialeurodes citri* Ashmead (citrus whitefly), *Trialeurodes abutiloneus* (bandedwinged whitefly) and *T. vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *N. nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicicada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

The present methods may be used to identify pesticidal genes that display activity against members from the order Hemiptera including: *Acrosternum hilare* Say (green stink bug), *Anasa tristis* De Geer (squash bug), *Blissus leucopterus* leucopterus Say (chinch bug), *Corythuca gossypii* Fabricius (cotton lace bug), *Cyrtopeltis modesta* Distant (tomato bug),

*Dysdercus suturellus* Herrich-Schäffer (cotton stainer), *Euschistus servus* Say (brown stink bug), *Euschistus variolarius* Palisot de Beauvois (one-spotted stink bug), *Graptostethus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper).

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used to identify novel pesticidal genes that encode polypeptides that protect any plant species from pest-related damage, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), *macadamia* (Macadamia integrifolia), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The article "a" and "an" are used herein to refer to one or more than one (i.e., to at least one) of the grammatical object of the article. By way of example, "an element" means one or more element.

EXPERIMENTAL

Example 1

Identification of Novel Cry8A/Cry8B Homologues

Isolation of *Bacillus thuringiensis* Plasmid DNA

*B. thuringiensis* strains from Dupont glycerol stocks were streaked onto LB agar plates. The following day a single colony from each strain was inoculated into 2 ml of TB media per well of a 48-well plate. The plates were incubated overnight at 28° C. and 250 rpm. The cells were harvested by centrifugation at 6,000×g for 10 minutes at room temperature. The cell pellets were resuspended by vortexing in P1 suspension buffer (Qiagen). Cells were lysed and neutralized with P2 and P3 buffers, respectively, and the lysates were transferred to TurboFilters (Qiagen) with vacuum applied. The filtrates were bound to QIAprep plates and washed with PB and PE buffers (Qiagen). The plasmid preparations were eluted with EB buffer and collected in 96-well plates.

Non-degenerate Oligonucleotide Primer Design

In order to identify Cry8A/Cry8B homologues, a pair of non-degenerate oligonucleotide primers was designed. Specifically, nucleotide sequences for all known Cry8A and Cry8B genes (i.e., the target group) were collected from public databases, and an alignment of these nucleotide sequences was prepared. The alignment included the nucleotide sequence for the Cry8Aa1 gene (i.e., the pesticidal gene of interest).

An initial primer length of 15 bp was selected, and a window of 15 contiguous nucleotides beginning at the 5' end of the Cry8Aa1 gene was viewed. Specifically, the nucleotide sequence within the window was reviewed to determine if the following sequence features were present:

1) does not have four or more contiguous identical nucleotide residues;

2) has no more than two guanine or cytosine residues within the last five residues of the 3' end of the nucleotide sequence;

3) has a melting temperature $T_m$ of between about 57° C. and about 61° C.;

4) does not form hairpin or dimer structures;

5) is present in all of the nucleotide sequences from the target group of pesticidal genes (i.e., the alignment); and, 6) is not conserved among nucleotide sequences from non-target group pesticidal genes.

If all sequence features were present, the nucleotide sequence within the window of nucleotides was selected for use an oligonucleotide primer. If the nucleotide sequence within the window did not possess the required sequence features, then an adjacent window of contiguous nucleotides was selected by moving 1 bp closer to the 3' end of the Cry8Aa1 gene, and the process was repeated. If the entire nucleotide sequence for the Cry8Aa1 gene was reviewed using a window of nucleotides equivalent in length to the initial primer length without identifying an appropriate oligonucleotide primer, then the window length was increased by 1 bp, and the nucleotide sequence for the Cry8Aa1 gene was screened as before. Additional rounds of screening using incrementally larger window lengths were performed as needed to identify an oligonucleotide primer that possesses all of the required sequence features. Both a forward and a reverse oligonucleotide primer were designed in accordance with the present methods. Furthermore, the forward and reverse primers were designed such that they were complementary to nucleotide sequences in the pesticidal gene of interest that are about 50 bp to about 150 bp apart.

The following non-degenerate oligonucleotide primer pair was designed for the identification of Cry8A/Cry8B homologues:

```
Forward primer: cry8AB_1f
AAATGCAGGAATATGGGTTGGA          (SEQ ID NO:5)

Reverse primer: cry8AB_1r
TCATTTGAATCTTCCACTGTTGTTC       (SEQ ID NO:6)
```

First Round of PCR Amplification: SYBR® Green

A first round of PCR amplification of the *B. thuringiensis* nucleic acid material was performed using the oligonucleotide primers designed as described above. Specifically, the *B. thuringiensis* plasmid preparations in 96-well plates were amplified by PCR under the following reaction conditions:

Template DNA amount: 100 ng

Primer amount: 7.5 nmole (5 μM×1.5 μl)

Volume of reaction mixture: 25 μl

AmpliTag® Gold DNA polymerase activation: 95° C. for 10 min

PCR cycle (40 cycles): 95° C. for 15 sec; 60° C. 1 min

PCR products from the first round of amplification were detected using a SYBR® Green fluorescent dye and the 7700 ABI Prism Sequence Detection System. A plasmid preparation from DuPont strain 1218-1 that comprises the Cry8Bb1 gene was used as a positive control. At the PCR conditions described above, the 1218-1 plasmid preparation produced a standard curve for PCR amplification in the 7700 ABI Prism Sequence Detection System, and a Ct value of approximately 13 was obtained for the positive control. A negative control comprising only the PCR reaction mixture without template DNA was tested and generated a Ct value of approximately 35. *B. thuringiensis* plasmid preparations that produced a Ct value of below 16 were selected for further analysis and designated SYBR® Green positives.

Glycerol stocks of *B. thuringiensis* strains for the SYBR® Green positives were streaked on LB agar plates and grown overnight. Single colonies were inoculated in 5 ml of TB media and incubated overnight at 28° C. and 250 rpm. Plasmid preparations from these cultures were prepared using a Qiagen Mini-Prep kit and used in a second round of PCR amplification.

Second Round of PCR Amplification: TaqMan® Analysis

The SYBR® Green positives were subjected to a second round of PCR amplification in accordance with TaqMan® protocols in order to eliminate known pesticidal genes. TaqMan® probes and primers were designed based on sequence information for known pesticidal genes, specifically Cry8Aa, Cry8Ba, Cry8Bb, and Cry8Bc genes. The following primers and probes were used for the second round of PCR amplification:

```
Cry8Aa:

Probe (36712):
TGAAATACCTCTAGATAGAACTGTACCGGTAGCTGA (SEQ ID NO:7)

Forward primer (36711):
ACATACAGCTCTCCAAGGGTGT              (SEQ ID NO:8)

Reverse primer (36713):
AGAAAGAATGGGAGGTAATATGAGATA         (SEQ ID NO:9)

Cry8Ba:

Probe (36715):
ATCCACTTGGCGCGGTAGATGTG             (SEQ ID NO:10)

Forward primer (36714):
GGCAACAACAGCTCAGCTTAC               (SEQ ID NO:11)

Reverse primer (36716):
AGGTGGACGAATAGCCGCT                 (SEQ ID NO:12)

Cry8Bb:

Probe (74500):
CCTTACTGTATATGCAATGGCAGCCAACCT      (SEQ ID NO:13)

Forward primer (74501):
CTTTTAGAGTGACAAATTTTGAAGTACCAT      (SEQ ID NO:14)

Reverse primer (74502):
ACGCGTCCTTTAATAACAGTAAATGA          (SEQ ID NO:15)

Cry8Bc:

Probe (74503):
TACACAGGCAGCCAACCTTCATTTACTGTT      (SEQ ID NO:16)

Forward primer (74504):
CAAATTTTGAAGTACCATTCCTTACAGT        (SEQ ID NO:17)

Reverse primer (74505):
CCAAAAATTGAAGCGTCCTTTAA             (SEQ ID NO:18)
```

Sequencing Characterization of Potential Novel Cry8A/Cry8B Homologues

*B. thuringiensis* strains that were not amplified in the second round of PCR amplification (i.e., TaqMan® negatives) were selected as potential novel Cry8A/Cry8B homologues and subjected to further PCR analysis with the following primers:

```
Cry8AB-74990:
ATGAGTCCAAATAATCAAAATG          (SEQ ID NO:19)

Cry8AB-73695:
TCTACGTCTACAATCAATTCTACAC       (SEQ ID NO:20)
```

After sequencing the full length genes, potential novel homologues were identified in *B. thuringiensis* strains Cry8AB001.1 (SEQ ID NO:1) and Cry8AB008.1 (SEQ ID NO:3). The amino acid sequences encoded by the nucleotide sequences of SEQ ID NO:1 and 3 are set forth in SEQ ID NO: 2 and 4, respectively.

Sequencing Characterization of Potential Novel Cry8A/Cry8B Homologues

Cloning of 88 kD Fragment of Potential Novel Cry8A/Cry8B Genes

PCR primers were designed for cloning an 88 kD fragment (including the toxin domain) from the N-terminus of the potential novel Cry8A/Cry8B genes. The following PCR primers were used:

```
Cry8AB-75576:
GGATCCATGAGTCCAAATAATCAAAATG    (SEQ ID NO:21)

Cry8AB-73694:
GCAGTGAATGCCTTGTTTACGAATAC      (SEQ ID NO:22)
```

The PCR products were cloned into a TA vector. Constructs containing the potentially novel Cry8A/Cry8B genes were then sequenced again.

Primary Sequence Analysis of Potential Novel Cry8A/Cry8B Genes

To assess the novelty of the selected sequences, the nucleic acid sequence data from the N-terminus and C-terminus (approximately 650 bp from each terminus) of the toxin domain for the potentially novel Cry8A/Cry8B homologues were analyzed using BLAST searches against known pesticidal genes from public *B. thuringiensis* databases and published patents. The entire 88 kD fragment for the potentially novel sequences was sequenced and cloned into an expression vector. Table 1 shows the percent identity of the toxin domain of the novel Cry8A/Cry8B genes and known Cry8 genes.

TABLE 1

Percent Identity of the Toxin Domain of Novel Cry8A/Cry8B Homologues

| | Cry8Aa | Cry8Ba | Cry8Bb | Cry8Bc | Cry8Ca | Cry8Da |
|---|---|---|---|---|---|---|
| Cry8AB001.1 (SEQ ID NO: 1) | 63.4 | 70.2 | 70.0 | 70.9 | 58.0 | 61.6 |
| Cry8AB008.1 (SEQ ID NO: 3) | 73.4 | 62.6 | 63.8 | 66.7 | 57.1 | 67.1 |

Secondary Sequence Analysis of Potential Novel Cry8A/Cry8B Genes

The sequence data for the entire 88 kD fragment of each of the potentially novel Cry8A/Cry8B homologues were analyzed using BLAST searches against known pesticidal genes from public *B. thuringiensis* databases and published patents. The percent identity of the 88 kD fragments relative to known pesticidal genes was used to further assess the novelty of the selected sequences.

Final Sequence Analysis of Potentially Novel Cry8A/Cry8B Genes

Sequences that were determined to be novel by the secondary sequence analysis were further analyzed by Southern blot and dot blot. Gene libraries for those *B. thuringiensis* strains that harbor potential novel Cry8A/Cry8B genes were generated, and the full-length sequence for each potentially novel gene was determined. Genome-walking experiments were performed to confirm the novelty of the identified sequences.

Expression of Novel Cry8A/Cry8B Genes and Bioassays for Pesticidal Activity

The DNA fragment representing 88 kDa for the novel Cry8A/Cry8B genes were cloned into pET20b expression vectors (Clontech). The His-Tag polypeptides encoded by the novel genes were purified using Talon Metal Affinity Resin (BD Bioscience Clontech) and used in bioassays for assessing pesticidal activity against western corn rootworm (WCRW), Colorado potato beetle (CPB), and southern corn rootworm (SCRW). Such bioassays are well known in the art. See, for example, Czapla and Lang (1990) *J. Econ. Entomol.* 83(6):2480-2485 and U.S. Pat. Nos. 6,570,005 and 6,339,144. The results of the bioassay are summarized below in Table 2.

TABLE 2

Pesticidal Activity of Novel Cry8A/Cry8B Toxins

| | Toxin Domain | Expression | Pesticidal Activity |
|---|---|---|---|
| Cry8AB001.1 (SEQ ID NO: 1) | Full | Yes | CPB active |
| Cry8AB008.1 (SEQ ID NO: 3) | Full | Yes | CPB active |

Example 2

Mixed Oligonucleotide Primer Methodology

Because it was difficult to design a single set of primers that is specific to the entire Cry2A group, a set of mixed oligonucleotide primers was designed. Specifically, oligonucleotide primers for each of the Cry2Aa, Cry2Ab, and Cry2Ac subgroups were designed, as described herein above. The primers for each subgroup were mixed and used in PCR to amplify nucleic acid material from various *B. thuringiensis* strains. PCR products were detected using SYBR® Green fluorescent dye, and Ct values were determined. *B. thuringiensis* strain DP2634, which comprises the Cry2Ab and Cry2Ac genes, and strain DP2639, which comprises the Cry2Aa gene, were used as positive controls. A reaction mixture without template DNA was used as a negative control.

The results of the PCR amplifications performed using the mixed primers and the individual primers for each subgroup are summarized in Table 3 below. The results obtained with the positive control strain DP2634 using the mixed primers were similar to those obtained with the individual primers for the Cry2Ab and Cry2Ac subgroups, indicating that the mixed primer methodology can be used to detect Cry2 genes. Moreover, the Ct values observed with strains DP6, DP25, and DP26 were approximately the same as those obtained for the positive control, indicating that these strains may contain novel Cry2A homologues.

TABLE 3

SYBR ® Green Results Using Cry2 Oligonucleotide Primers

| | $C_T$ value | | | |
|---|---|---|---|---|
| Strain ID | Cry2 primers Aa + Ab + Ac (Mix) | Cry2 primers Aa | Cry2 primers Ab | Cry2 primers Ac |
| DP6 | 16.7 | 16.3 | 15.1 | 21.4 |
| DP25 | 15.3 | 16.8 | 16.8 | 25.2 |
| DP26 | 15.7 | 16.6 | 14.9 | 23.7 |
| DP2634 | 16.1 | | 15.1 | 15.3 |
| DP2639 | | 15.1 | | |
| No DNA | 25 | 29 | 30.1 | 26.2 |

Example 3

Degenerate Oligonucleotide Primer Design

A set of degenerate oligonucleotide primers was designed for the Cry2A target group of pesticidal genes, as described above. Specifically, an alignment of various Cry2A sequences was generated using sequence information from public databases. Windows of contiguous nucleotides were reviewed, and a sequence that is conserved among all nucleotide sequences from the target group (i.e., the alignment) was identified. A set of all possible forward and reverse degenerate oligonucleotide primers based on these conserved sequences was designed:

| Degenerate Oligonucleotide Primers (Forward Primers) | |
|---|---|
| **GCGAATATAAGGGAGTTTAATCAACA** | (SEQ ID NO:23) |
| **GCAAATGTAGAGGAATTTAATCGACA** | (SEQ ID NO:24) |
| **GCAAATGTAGAAGAGTTTAATCGACA** | (SEQ ID NO:25) |
| **GCGAATGTGGCAGAGTTTAATCGACA** | (SEQ ID NO:26) |
| GCGAATATAATGGAGTTTAATCAACA | (SEQ ID NO:27) |
| GCGAATATAACGGAGTTTAATCAACA | (SEQ ID NO:28) |
| GCGAATATAAAGGAGTTTAATCAACA | (SEQ ID NO:29) |
| GCAAATGTAGTGGAATTTAATCGACA | (SEQ ID NO:30) |
| GCAAATGTAGCGGAATTTAATCGACA | (SEQ ID NO:31) |
| GCAAATGTAGGGGAATTTAATCGACA | (SEQ ID NO:32) |
| GCAAATGTAGTAGAGTTTAATCGACA | (SEQ ID NO:33) |
| GCAAATGTAGCAGAGTTTAATCGACA | (SEQ ID NO:34) |
| GCAAATGTAGGAGAGTTTAATCGACA | (SEQ ID NO:35) |
| GCGAATGTGGTAGAGTTTAATCGACA | (SEQ ID NO:36) |
| GCGAATGTGGGAGAGTTTAATCGACA | (SEQ ID NO:37) |
| GCGAATGTGGAAGAGTTTAATCGACA | (SEQ ID NO:38) |

| Degenerate Oligonucleotide Primers (Reverse Primers) | |
|---|---|
| **ACCCCAGTTCCAGATACAAGGATA** | (SEQ ID NO:39) |
| **ACCCCAGTTCCGTGTGCAAGGATA** | (SEQ ID NO:40) |
| **ACCCCAGTTCCAGATACAACGCTA** | (SEQ ID NO:41) |
| **AACCCAGTTCCAGATGCAAGGATA** | (SEQ ID NO:42) |
| **ATCCCAGTTCCAGATGCAAGGATA** | (SEQ ID NO:43) |
| **ACCACAGTTCCAGATGCAAGGCTA** | (SEQ ID NO:44) |
| AACCCAGTTCCAGATACAAGGATA | (SEQ ID NO:45) |
| AACCCAGTTCCAGATGCAAGGATA | (SEQ ID NO:46) |
| ATCCCAGTTCCAGATACAAGGATA | (SEQ ID NO:47) |
| ATCCCAGTTCCAGATGCAAGGATA | (SEQ ID NO:48) |
| AGCCCAGTTCCAGATACAAGGATA | (SEQ ID NO:49) |
| AGCCCAGTTCCAGATGCAAGGATA | (SEQ ID NO:50) |

-continued

| Degenerate Oligonucleotide Primers (Reverse Primers) | |
|---|---|
| ACCCCAGTTCCAGATACAAGGATA | (SEQ ID NO:51) |
| ACCCCAGTTCCAGATGCAAGGATA | (SEQ ID NO:52) |

The oligonucleotide primers in bold were mixed and used in PCR to amplify nucleic acid material from various *B. thuringiensis* strains essentially as described in Example 1.

Example 4

Design of Positive Controls for PCR Amplifications

Artificial positive controls for Cry3A and Cry3C genes were developed based on the oligonucleotide primer sequences designed for each of these genes. Specifically, an insert representing approximately 100 bp of Cry3A and Cry3C genes and comprising the forward primer and the reverse primer was designed and cloned into the pET28a vector. These constructs were amplified by PCR using the Cry3A or Cry3C oligonucleotide primers. PCR products were detected using SYBR® Green, and Ct values were determined. The Cry3A and Cry3C artificial positive controls produced Ct values of 13.3 and 11.4, respectively, compared with a Ct value of 40 for the negative control (pET28 without any insert), demonstrating that these artificial sequences can be used successfully as positive controls. Ct values around 11 to 16 are considered positive for homologue identification.

Cry3A:

Cry3A1F (forward primer):
AATCCTGTGAGTTCACGAAATCC (SEQ ID NO:53)

Cry3A1R (reverse primer):
TTGCAAACGAAGGCATTGAATTA (SEQ ID NO:54)

Cry3A1 Insert:
GATCCAATCCTGTGAGTTCACGAAATCCATGGGCAT (SEQ ID NO:55)
GAGTCCAAATAATCAAAATGAATATGAAATTATAGA
TGCTAATTCAATGCCTTCGTTTGCAAC Cry3C:

Cry3C1F (forward primer):
GGCCAGGTGAAGACCCTTTAA (SEQ ID NO:56)

Cry3C1R (reverse primer):
TTTGTCCCATGAATCCAATGC (SEQ ID NO:57)

Cry3C1 Insert:
GATCCGGCCAGGTGAAGACCCTTTAAATGGGCATGA (SEQ ID NO:58)
GTCCAAATAATCAAAATGAATATGAAATTATAGATG
CGCATTGGATTCATGGGACAAAC All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for identifying novel homologues of a target group of pesticidal genes of interest, said method comprising:

a) designing at least one pair of oligonucleotide primers that is specific for said target group of pesticidal genes, said pair of primers comprising a forward primer and a reverse primer, wherein said designing comprises i) preparing an alignment of nucleotide sequences for the target group of pesticidal genes, said alignment comprising a nucleotide sequence for a reference pesticidal gene of interest from the target group;

ii) selecting an initial primer length, wherein said initial primer length is between about 15 bp and 30 bp;

iii) performing a first round of screening for an oligonucleotide primer sequence, said screening comprising viewing an initial window of contiguous nucleotides within said nucleotide sequence for said reference pesticidal gene of interest, wherein said initial window is initiated at the 5' end of the nucleotide sequence for said reference pesticidal gene of interest and is equivalent in length to the initial primer length;

iv) determining if the nucleotide sequence within said initial window has the sequence features of 1-6 below;

(1) does not have four or more contiguous identical nucleotide residues;

(2) has no more than two guanine or cytosine residues within the last five residues of the 3' end of the nucleotide sequence;

(3) has a melting temperature ($T_m$) of between about 50° C. and 65° C. wherein said $T_m$ is calculated using Formula I below:

$$T_m=(EH^o/[ES^o+(R\times\ln(Ct))]-273.15+16.6\log([X]))\times 1.1144-14.964$$

wherein,

EH° (enthalpy)=ΣΔH;

ES° (entropy)=ΣΔS+0.368×19×1.585;

R (molar gas constant)=1.987;

Ct (total primer concentration)=log(0.00000005/4)×1000; and,

X (salt concentration [K+])=0.05;

(4) does not form hairpin or dimer structures;

(5) is present in all nucleotide sequences of said alignment; and, (6) is not conserved among non-target group pesticidal genes, wherein a nucleotide sequence that is not conserved among non-target group pesticidal genes differs from each of the non-target group pesticidal genes by at least two nucleotide residues;

v) selecting said nucleotide sequence within said initial window for use as an oligonucleotide primer if all of the sequence features of step iv) are present;

vi) selecting an adjacent window of contiguous nucleotides by moving said first window toward the 3' end of said nucleotide sequence for the reference pesticidal gene of interest by one base pair if said nucleotide sequence within said initial window does not have all of the sequence features of step iv), wherein said adjacent window is equivalent in length to the initial primer length;

vii) repeating steps iv)-vi) with said adjacent window until a nucleotide sequence with all of the sequence features of step iv) is identified or until the entire nucleotide sequence for the reference pesticidal gene of interest is screened; and, viii) performing additional rounds of screening comprising repeating steps iii)-vii) if no nucleotide sequence with all of the sequence features of iv) is identified, wherein the length of said initial window is increased by one base pair in each additional round of screening;

b) obtaining a first sample of nucleic acid material from a microorganism of interest;

c) mixing said first sample of nucleic acid material with said at least one pair of oligonucleotide primers specific for said target group of pesticidal genes and a thermostable DNA polymerase under conditions that are suitable for amplification by polymerase chain reaction (PCR);

d) performing a first round of PCR and detecting PCR amplification products, thereby determining if PCR products are produced in the first round of PCR;

e) obtaining a second sample of nucleic acid material from the microorganism if PCR amplification products are detected in the first round of PCR;

f) subjecting the second sample of nucleic acid material to a second round of amplification by PCR using pairs of oligonucleotide primers that are specific for all known pesticidal genes in the target group, wherein said pairs of oligonucleotide primers specific for known pesticidal genes in the target group comprise nucleotide sequences that are different from the nucleotide sequences for said oligonucleotide primers of (a);

g) detecting PCR amplification products from the second round of PCR, thereby determining if PCR products are produced in the second round of PCR;

h) obtaining a third sample of nucleic acid material from the microorganism if PCR products are detected in the first round of PCR and PCR products are not detected in the second round of PCR, wherein a microorganism that comprises nucleic acid material that is amplified in the first round of PCR and is not amplified in the second round of PCR comprises a putative novel homologue of the target group of pesticidal genes;

i) subjecting the third sample of nucleic acid material to a third round of PCR using at least one pair of oligonucleotide primers to clone the putative novel homologue; and, j) analyzing the putative novel homologue of the target group of pesticidal genes of interest.

2. The method of claim 1, wherein the microorganism of interest comprises a *Bacillus thuringiensis* strain.

3. The method of claim 2, wherein obtaining a first, second, and third sample of nucleic acid material comprises preparing plasmid DNA from the *Bacillus thuringiensis* strain.

4. The method of claim 1, wherein said target group of pesticidal genes of interest comprises *Bacillus thuringiensis* Cry genes.

5. The method of claim 4, wherein said *Bacillus thuringiensis* Cry genes are Cry2, Cry3, or Cry8 genes.

6. The method of claim 1, wherein said first and said second round of PCR comprise performing quantitative real-time PCR (RT-PCR).

7. The method of claim 6, wherein said first round of PCR is performed in the presence of a fluorescent entity, said fluorescent entity being capable of indicating the presence of PCR products and providing a signal related to the quantity of the PCR products.

8. The method of claim 7, wherein said fluorescent entity is a dye.

9. The method of claim 6, wherein said second round of PCR is performed in the presence of a nucleic acid probe, said probe comprising a fluorescent dye and a quenching dye.

10. The method of claim 1, wherein analyzing the putative novel homologue of the target group of pesticidal genes comprises nucleotide sequence analysis.

11. The method of claim 1, wherein said $T_m$ is between about 57° C. and 61° C.

12. The method of claim 1, wherein determining if a nucleotide sequence within a window is not conserved among non-target group pesticidal genes comprises searching the full-length sequence of each gene from the non-target group pesticidal genes.

13. A method for identifying novel homologues of a target group of pesticidal genes of interest, said method comprising:

a) designing at least two pairs of oligonucleotide primers, wherein each pair of primers is specific for a distinct sub-group of the target group of pesticidal genes, said pairs of primers comprising a forward primer and a reverse primer, wherein at least one of said pairs of oligonucleotide primers is designed by a method comprising:

i) dividing the target group of pesticidal genes into at least two sub-groups of pesticidal genes;
ii) preparing an alignment of nucleotide sequences for a sub-group of the target group of pesticidal genes of interest, said alignment comprising a nucleotide sequence for a reference pesticidal gene of interest from the sub-group of pesticidal genes;
iii) selecting an initial primer length, wherein said initial primer length is between about 15 bp and 30 bp;
iv) performing a first round of screening for an oligonucleotide primer sequence, said screening comprising viewing an initial window of contiguous nucleotides within said nucleotide sequence for said reference pesticidal gene of interest, wherein said initial window is initiated at the 5' end of the nucleotide sequence for said reference pesticidal gene of interest and is equivalent in length to the initial primer length;
v) determining if the nucleotide sequence within said initial window has the sequence features of 1-6 below;
(1) does not have four or more contiguous identical nucleotide residues;
(2) has no more than two guanine or cytosine residues within the last five residues of the 3' end of the nucleotide sequence;
(3) has a melting temperature ($T_m$) of between about 50° C. and 65° C. wherein said $T_m$ is calculated using Formula I below:

$$T_m=(EH°/[ES°+(R\times\ln(Ct))]-273.15+16.6\log([X]))\times 1.1144-14.964$$

wherein,
EH° (enthalpy)=ΣΔH;
ES° (entropy)=ΣΔS+0.368×19×1.585;
R (molar gas constant)=1.987;
Ct (total primer concentration)=log(0.00000005/4)×1000; and,
X (salt concentration [K+])=0.05;
(4) does not form hairpin or dimer structures;
(5) is present in all nucleotide sequences of said alignment; and,
(6) is not conserved among non-target group pesticidal genes, wherein a nucleotide sequence that is not conserved among non-target group pesticidal genes differs from each of the non-target group pesticidal genes by at least two nucleotide residues;
vi) selecting said nucleotide sequence within said initial window for use as an oligonucleotide primer if all of the sequence features of step v) are present;
vii) selecting an adjacent window of contiguous nucleotides by moving said initial window toward the 3' end of said nucleotide sequence for the reference pesticidal gene of interest by one base pair if said nucleotide sequence within said initial window does not have all of the sequence features of step v), wherein said adjacent window is equivalent in length to the initial primer length;
viii) repeating steps v)-vii) with said adjacent window until a nucleotide sequence with all of the sequence features of step v) is identified or until the entire nucleotide sequence for the reference pesticidal gene of interest is screened; and,
ix) performing additional rounds of screening comprising repeating steps iv)-viii) if no nucleotide sequence with all of the sequence features of v) is identified, wherein the length of said initial window is increased by one base pair in each additional round of screening;

b) generating a mixture of the pairs of oligonucleotide primers of (a);
c) obtaining a first sample of nucleic acid material from a microorganism of interest;
d) mixing said first sample of nucleic acid material with said mixture of oligonucleotide primers and a thermostable DNA polymerase under conditions that are suitable for amplification by polymerase chain reaction (PCR);
e) performing a first round of PCR and detecting PCR amplification products, thereby determining if PCR products are produced in the first round of PCR;
f) obtaining a second sample of nucleic acid material from the microorganism if PCR amplification products are detected in the first round of PCR;
g) subjecting the second sample of nucleic acid material to a second round of amplification by PCR using pairs of oligonucleotide primers that are specific for all known pesticidal genes in the target group, wherein said pairs of oligonucleotide primers specific for known pesticidal genes in the target group comprise nucleotide sequences that are different from the nucleotide sequences for said oligonucleotide primers of (a);
h) detecting PCR amplification products from the second round of PCR, thereby determining if PCR products are produced in the second round of PCR;
i) obtaining a third sample of nucleic acid material from the microorganism if PCR products are detected in the first round of PCR and PCR products are not detected in the second round of PCR, wherein a microorganism that comprises nucleic acid material that is amplified in the first round of PCR and is not amplified in the second round of PCR comprises a putative novel homologue of the target group of pesticidal genes;
j) subjecting the third sample of nucleic acid material to a third round of PCR using at least one pair of oligonucleotide primers to clone the putative novel homologue; and,
k) analyzing the putative novel homologue of the target group of pesticidal genes of interest.

* * * * *